US009447174B2

(12) United States Patent
Coljee et al.

(10) Patent No.: US 9,447,174 B2
(45) Date of Patent: *Sep. 20, 2016

(54) METHODS FOR PRODUCING RECOMBINANT PROTEINS

(71) Applicant: Excelimmune Liquidating Trust, Hudson, MA (US)

(72) Inventors: Vincent W. Coljee, Watertown, MA (US); Gwendolyn M. Wilmes, Belmont, MA (US); Stuart Hicks, North Andover, MA (US); Kimberly L. Carey, Winchester, MA (US); Elizabeth R. Reczek, Weston, MA (US)

(73) Assignee: Excelimmune Liquidating Trust, Hudson, MA (US)

( * ) Notice: Subject to any disclaimer, the term of this patent is extended or adjusted under 35 U.S.C. 154(b) by 232 days.

This patent is subject to a terminal disclaimer.

(21) Appl. No.: 14/037,833

(22) Filed: Sep. 26, 2013

(65) Prior Publication Data

US 2014/0127743 A1 May 8, 2014

Related U.S. Application Data

(60) Division of application No. 13/495,993, filed on Jun. 13, 2012, now Pat. No. 8,617,881, which is a continuation of application No. PCT/US2011/061092, filed on Nov. 16, 2011.

(60) Provisional application No. 61/414,225, filed on Nov. 16, 2010.

(51) Int. Cl.
*C07K 16/12* (2006.01)
*C07K 16/00* (2006.01)
*C12N 15/10* (2006.01)
*C12N 15/67* (2006.01)

(52) U.S. Cl.
CPC ........... *C07K 16/1271* (2013.01); *C07K 16/00* (2013.01); *C12N 15/1093* (2013.01); *C12N 15/67* (2013.01); *C12N 2799/025* (2013.01)

(58) Field of Classification Search
CPC .................... C12N 15/1093; C12N 2799/025; C12N 15/67; C07K 16/1271; C07K 16/00
USPC ......................................................... 435/34
See application file for complete search history.

(56) References Cited

U.S. PATENT DOCUMENTS

| 4,937,190 A | 6/1990 | Palmenberg et al. |
| 4,959,317 A | 9/1990 | Sauer |
| 5,654,182 A | 8/1997 | Wahl et al. |
| 5,686,120 A | 11/1997 | Mertz et al. |
| 5,780,225 A | 7/1998 | Wigler et al. |
| 5,914,267 A | 6/1999 | Mertz et al. |
| 6,060,273 A | 5/2000 | Dirks et al. |
| 6,136,597 A | 10/2000 | Hope et al. |
| 6,852,510 B2 | 2/2005 | Bremel et al. |
| 7,378,273 B2 | 5/2008 | Bleck |
| 7,910,332 B2 | 3/2011 | Nielsen et al. |
| 2003/0157641 A1 | 8/2003 | Reff et al. |
| 2009/0111142 A1 | 4/2009 | Nielsen et al. |
| 2009/0191588 A1* | 7/2009 | Hermens et al. ............ 435/69.1 |

FOREIGN PATENT DOCUMENTS

| JP | 2006-515520 A | 6/2006 |
| WO | WO 98/41645 | 9/1998 |
| WO | WO 99/14310 | 3/1999 |
| WO | WO 01/07572 | 2/2001 |
| WO | WO 2004/061104 | 7/2004 |
| WO | WO 2005/042774 | 5/2005 |
| WO | WO 2009/129814 | 10/2009 |

OTHER PUBLICATIONS

Bløet al., "Expanding the spectrum of genetic elements transferable by retroviral vectors," *DNA Cell Biol.*, 26(11): 773-779, 2007.
Bohenzky et al., "Sequence and symmetry requirements within the internal palindromic sequences of the adeno-associated virus terminal repeat," *Virology*, 166(2): 316-327, 1988.
Crawford, VP, "Nash equilibrium and evolutionary stability in large- and finite-population "playing the field" models," *J. Theor Biol.*, 145(1): 83-94, 1990.
De Jesus et al., "Manufacturing recombinant proteins in kg-ton quantities using animal cells in bioreactors," *Eur J Pharm Biopharm*, 78(2): 184-188, 2011.
Gorman et al., "Site-specific gene targeting for gene expression in eukaryotes," *Curr Opin Biotechnol.*, 11(5): 455-460, 2000.
Gray et al., "Periplasmic production of correctly processed human growth hormone in *Escherichia coli*: natural and bacterial signal sequences are interchangeable," *Gene*, 39(2-3): 247-254, 1985.
Groth et al., "A phage integrase directs efficient site-specific integration in human cells," *Proc Natl Aced Sci USA*, 97(11): 5995-6000, 2000.
Hopkins et al., "Optimizing transient recombinant protein expression in mammalian cells," *Methods Mol Biol.*, 801: 251-268, 2012.
Huang et al., "An efficient and targeted gene integration system for high-level antibody expression", J. Immunol. Meth., 322:28-39 (2007).
Hüser et al., "Integration preferences of wildtype AAV-2 for consensus rep-binding sites at numerous loci in the human genome," *PLoS Pathog.*, 6(7): e1000985, 2010.
Jostock et al., "Combination of the 2A/furin technology with an animal component free cell line development platform process," *Appl Microbiol Biotechnol.*, 87(4): 1517-1524, 2010.
Kotin, RM, "Prospects for the use of adeno-associated virus as a vector for human gene therapy," *Hum Gene Ther.*, 5(7): 793-801, 1994.
Lessard, S, "Long-term stability from fixation probabilities in finite populations: new perspectives for ESS theory," *Theor Popul. Biol.*, 68(1): 19-27, 2005.

(Continued)

*Primary Examiner* — Larry Riggs
*Assistant Examiner* — Karla Dines
(74) *Attorney, Agent, or Firm* — Choate, Hall & Stewart LLP; David E. Shore; Charles E. Lyon

(57) ABSTRACT

Methods for producing recombinant cell populations are disclosed. The disclosed methods may be used to produce therapeutic polyclonal proteins.

34 Claims, 21 Drawing Sheets

(56) References Cited

OTHER PUBLICATIONS

Martial et al., "Human growth hormone: complementary DNA cloning and expression in bacteria," *Science*, 205(4406): 602-607, 1979.

Migliaccio et al., "Stable and unstable transgene integration sites in the human genome: extinction of the Green Fluorescent Protein transgene in K562 cells," *Gene* 256(1-2): 197-214, 2000.

Mitchell et al., "Retroviral DNA integration: ASLV, HIV, and MLV show distinct target site preferences," *PLos Biol.*, 2(8): E234, 2004.

Nielsen et al., "Single-Batch Production of Recombinant Human Polyclonal Antibodies," *Mol Biotechnol*, 45: 257-266, 2010.

Nowak et al., "Emergence of cooperation and evolutionary stability in finite populations," *Nature* 428(6983): 646-650, 2004.

Olsen, JC, "Gene transfer vectors derived from equine infectious anemia virus," *Gene Ther.*, 5(11): 1481-1487, 1998.

Poste et al., "Interactions among clonal subpopulations affect stability of the metastatic phenotype in polyclonal populations of B16 melanoma cells," *Proc Natl Aced Sci USA*, 78(10): 6226-6230, 1981.

Smith, JM, "The theory of games and the evolution of animal conflicts," *J. Theor Biol.*, 47(1): 209-221, 1974.

Smith, RH, "Adeno-associated virus integration: virus versus vector," *Gene Ther.*, 15(11): 817-822, 2008.

Wang, et al., "Rescue and replication signals of the adeno-associated virus 2 genome," *J. Mol Biol.*, 250(5): 573-580, 1995.

Weitzman et al., "Adeno-associated virus (AAV) Rep proteins mediate complex formation between AAV DNA and its integration site in human DNA," *Proc Natl Aced Sci USA*, 91(13): 5808-5812, 1994.

Würtele et al., "Illegitimate DNA integration in mammalian cells," *Gene Ther.*, 10(21): 1791-1799, 2003.

Zhou et al., "Generation of stable cell lines by site-specific integration of transgenes into engineered Chinese hamster ovary strains using an FLP-FRT system," *J. Biotechnol.*, 147(2): 122-129, 2010.

Zhou et al., "In vitro packaging of adeno-associated virus DNA," *J. Virol.*, 72(4): 3241-3247, 1998.

Zwizinski et al., "Purification and characterization of leader (signal) peptidase from *Escherichia coli*," *J. Biol. Chem.*, 255(16): 7973-7977, 1980.

International Search Report for PCT/US2011/061092, mailed Jun. 27, 2012.

Written Opinion of the International Searching Authority for PCT/US2011/061092, mailed Jun. 27, 2012.

Howden, S. E., The transient expression of mRNA coding for Rep protein from AAV facilitates targeted plasmid integration, J. Gene Med., 10:42-50 (2007).

Howden, S.E., Site-specific, Rep-mediated integration of the intact beta-globin locus in the human erythroleukaemic cell line K562, Gene Therapy, 15:1372-1383 (2008).

Surosky, R.T., Adeno-Associated Virus Rep Proteins Target DNA Sequences to a Unique Locus in the Human Genome, J. Virol., 71(10):7951-7959 (1997).

Yue, Y., Functional Differentiation Between Rep-Mediated Site-Specific Integration and Transcriptional Repression of the Adeno-Associated Viral p5 Promoter, Human Gene Therapy, 21:728-738 (2010).

DeMaria et al., "Accelerated clone selection for recombinant CHO cells using a FACS-based high-throughput screen," Biotechnol. Prog. Mar.-Apr.(2):465-72, Epub Jan. 30, 2007.

Gaillet et al., "High-level recombinant protein production in CHO cells using lentiviral vectors and the cumate gene-switch," Biotechnol. and Bioengineering 106(2):203-215 (2010).

Declaration of Elizabeth Reczek dated Jul. 30, 2013 together with Exhibit A (Assignment of U.S. Appl. No. 13/495,993 from Dr. Coljee to Excelimmune dated Jun. 29, 2012) and Exhibit B (Email correspondence with Dr. Coljee from May 16, 2013 to Jul. 22, 2013).

Mizuarai, S. et al., Integrase-mediated nonviral gene transfection with enhanced integration efficiency, J. Biosci. Bioeng., 88(5):461-7 (1999).

Recchia, A. et al., Site-specific integration of functional transgenes into the human genome by adeno/AAV hybrid vectors, Mol. Ther., 10(4):660-70 (2004).

Zeyda, M. et al., Optimization of sorting conditions for the selection of stable, high-producing mammalian cell lines, Biotechnol. Prog., 15(5):953-7 (1999).

\* cited by examiner

200
METHODS FOR PRODUCING RECOMBINANT PROTEINS

CROSS-REFERENCE TO RELATED APPLICATIONS

This application is a divisional of U.S. application Ser. No. 13/495,993, filed Jun. 13, 2012, which is a continuation of International Application No. PCT/US2011/061092, filed Nov. 16, 2011, which claims the benefit of and priority to U.S. Provisional Application No. 61/414,225, filed Nov. 16, 2010; the disclosure of each of which is incorporated herein by reference in its entirety.

FIELD OF THE INVENTION

The field of the invention is molecular biology and immunology. More particularly, the field is the production of recombinant polyclonal proteins such as antibodies, vaccines, and T cell receptors.

BACKGROUND

Since the production of tissue plasminogen activator (tPa) as the first marketed recombinant therapeutic drug in 1987, the methods for producing recombinant proteins have remained largely unchanged. For example, Chinese Hamster Ovary (CHO) cells have been the cell line of choice for creating stable recombinant polypeptide production cell lines. CHO cells, however, like other cancer-derived cell lines, are inherently unstable because of their aneuploidy and predilection for chromosomal rearrangements making the process of finding stable clones difficult. Although relative production increases in the last 25 years have been substantial from 50-100 mg/l to 1-5 g/l, the yield increases can be attributed to process improvements rather than improvements on the technology used (see, e.g., the review by De Jesus & Wurm, European Journal of Pharmaceutics and Biopharmaceutics 78 (2011) 184-188). Thus, current methodology for producing recombinant proteins relies on the creation of a clonal cell line that stably produces protein at high expression levels. This process is labor intensive and can take a year or longer for creation of a suitable production-based cell line for production.

Alternatively, transient gene expression may be used to achieve a transient moderate yield of a recombinant polypeptide (e.g., reviewed by Hopkins et al., Methods Mol Biol, 2012, 801:251-68). Although this methodology is simpler and more rapid (e.g., with the possibility to produce at a gram per liter in a two-week period), the possibility to scale this technology beyond 100 liters does not yet exist. Thus, there is a need for a scalable system for generating stable recombinant polypeptide producing cells in a more rapid and cost effective manner.

Multi-component therapies based on recombinant polyclonal proteins represent promising new drugs for the treatment of various diseases and disorders including infectious diseases, cancer, neurological disorders, inflammation and immune disorders, and cardiovascular diseases. Polyclonal proteins, such as vaccines and polyclonal antibodies, are uniquely suited to treat pathogens and other disease causing agents because they simultaneously target multiple epitopes and, therefore, decrease the selective pressure for the development of resistant strains. For example, the effectiveness of hyperimmune immunoglobulins is rarely affected by mutations in the target pathogen, because these immunoglobulins consist of complex pools of antibodies derived from individuals with high titers against a specific infectious disease. Exemplary hyperimmune immunoglobulins include CytoGAM® (which targets cytomegalovirus), VZIG (which targets varicella virus), HBIG (which targets hepatitis B virus), and RIG (which targets rabies virus). Despite their effectiveness, however, hyperimmune immunoglobulins are subject to batch-to-batch variability, limited availability, and carry the risk of blood-borne disease transmission. In addition, relatively high doses are needed because only a small percentage of the component antibodies recognize epitopes in the agent of interest.

Monoclonal antibody therapies have also been developed; however, the use of monoclonal antibodies for the treatment of infectious disease has so far been largely unsuccessful. Currently, the only monoclonal antibody on the market against an infectious disease agent is Synagis (palivizumab), which targets Respiratory Syncytial Virus (RSV). Although Synagis has successfully prevented infection in premature infants, its efficacy in other applications, such as prevention of disease in children with cystic fibrosis or as a treatment in adults with stem cell transplants has been unclear. In other studies, some monoclonal antibody therapies are able to provide a degree of protection in animal models of infectious disease, but the required doses are often high. Further, a high degree of genetic diversity and variable expression among bacterial strains reduces the likelihood that a single monoclonal treatment will be effective against all strains.

Although immunoglobulins (e.g., passive immunotherapy) have been employed in human medicine since the late 1800s and monoclonal antibodies since the 1980s, human recombinant polyclonal antibodies (HRPAs) are a relatively new form of immunotherapy. Like intravenous immunoglobulins (IVIGs), HRPAs are able to overcome multiple mutational challenges without significant loss of efficacy, thereby reducing selective pressure that leads to the emergence of resistant strains. However, unlike serum derived polyclonal immunoglobulins, the recombinant nature of HRPA therapy avoids the variability in composition and availability, as well as the risk of blood borne disease transmission inherent in IVIG preparations. In addition, synergistic activity of a large group of highly specific antibodies within an HRPA may enhance passive immunotherapy efficacy far beyond what can be accomplished with monoclonals or IVIGs.

A number of methods for the manufacture of recombinant antibodies have been described previously to generate large amounts of recombinant protein for clinical uses. Many of these methods rely on transfection of plasmid DNA followed by random integration of the gene into the host cell genomic DNA, selection of individual progenitor clones with high expression levels, and expansion to generate master cell lines for production. Random integration into the genome can result in positional effects due to insertion in "non-permissive" regions of the genome. Once highly expressing clones are obtained, expression may be unstable, decreasing over time due to gene silencing mechanisms such as methylation or heterochromatin formation. Bulk transformed cell populations are also used, but only for selecting specific highly stable producer cell lines. The number of methods for production of recombinant polyclonal proteins is more limited. Moreover, it is well-understood in the field of recombinant protein expression that a mixture of cell lines is unstable (see, e.g., Migliaccio et al., Gene 256 (2000) 197-214, which describes that integration of extraneous DNA into a cell's genome is often inherently unstable and Nielsen et al., Mol Biotechnol (2010) 45:257-266, which discusses instability and bias of antibody producing cells in mixed cell lines).

To circumvent the positional effects observed with random integration techniques, methods for site-specific integration of expression constructs into the genome have been described (see, e.g., U.S. Pat. Nos. 4,959,317 and 5,654,182; WO 98/41645; WO 01/07572; WO 2005/042774 and WO 2004/061104). For example, patent application WO 2004/061104 describes a method for the production of recombinant polyclonal proteins, including antibodies, using a library of vectors in such a way that relative expression levels of these vectors are maintained over time. This method makes use of a site-specific Flp recombinase to ensure that integration of the recombinant protein expression cassette occurs at FRT site(s) present in the genome that is presumed to be permissive for gene expression. However, the use of site-specific Flp recombinase for the production of polyclonal antibodies can result in low expression levels during production, loss of expression, and genome instability similar to that observed with randomly integrated DNA because (a) FRT site(s) have to be engineered into the genome of the expression cell line. To address this potential for instability and low inconsistent expression, a cell line can be selected for with the FRT site located in a particularly permissive site that confers high stability and expression (Zhou et al., J Biotech 147 (2010) 122-129).

As such, there remains an ongoing need for improved recombinant polyclonal proteins that are useful as therapeutic agents, and methods for producing stable populations of recombinant polyclonal proteins.

SUMMARY

The invention is based, in part, on the discovery of methods for producing stable cell populations that do not require clonal selection of an individual progenitor cell clone or the production of an individual cell line. Stability of cell populations expressing a single recombinant polypeptide or multiple recombinant polypeptides as disclosed herein is achieved by using large populations of transformed cells. Surprisingly, using the disclosed methods, stability of cell populations expressing a single recombinant polypeptide or multiple recombinant polypeptidesis achieved and can be maintained without a bias to certain cells in the population over time.

As disclosed herein, the use of large transformed cell populations provide a surprising advantage for preparing and maintaining stable cell populations (e.g., cell populations expressing a single recombinant polypeptide or cell populations expressing multiple recombinant polypeptides). In an exemplary embodiment, a stable cell population is generated in accordance with certain mathematical limitations as outlined in the evolutionary dynamics of large, but finite populations. Stable transformed cell populations expressing a single recombinant polypeptide can be obtained by transforming a population of host cells (e.g., by preferential integration) of at least one vector comprising at least one copy of a nucleic acid sequence encoding a protein of interest into the host cell genomic DNA to generate large populations of individual transformed cells and maintaining the population of host cells. In an exemplary embodiment, stable transformed cell populations expressing multiple recombinant polypeptides can be obtained by first generating large populations of individual transformed cells (e.g., by preferential integration) and then mixing large numbers of individual cell populations (e.g., about 100,000 or more cells per individual cell population). Because large populations of individual transformed cells are used to generate stable polyclonal cell populations, the disclosed methods do not require banking of individual cells lines. Moreover, the stable cell populations can be maintained in the presence of non-transformed cells without a bias to certain cells in the population over time. As a result, the disclosed methods are faster, more efficient and less expensive than methods requiring the selection of stable clones.

The disclosed methods for producing cell populations may be used for the large scale production and manufacture of therapeutic recombinant proteins and therapeutic recombinant polyclonal protein compositions, such as recombinant polyclonal vaccines, recombinant polyclonal antibody compositions, and recombinant polyclonal T-cell receptor compositions.

In one aspect, provided herein is a method for producing a cell population. The cell population may be a "monoclonal" cell population (e.g., the cell population produces a single protein of interest) or a "polyclonal" cell population (e.g., the cell population produces a plurality of proteins of interest, e.g., a polyclonal antibody composition). The method comprises the steps of (a) transforming a population of host cells with at least one vector comprising at least one copy of a nucleic acid sequence encoding a protein of interest that integrates into the genomic DNA of a subset of the population of host cells thereby generating a population of host cells capable of producing the protein of interest and (b) maintaining the population of host cells to produce the protein of interest. The population of host cells may include both transformed host cells and non-transformed host cells and does not require clonal selection of an individual progenitor cell clone for generation and/or maintenance of the cell population. In an exemplary embodiment, the population of host cells are transformed using vectors that preferentially integrate into the host cell genomic DNA.

In certain embodiments, the method may further comprise the steps of (c) repeating steps (a) and (b) at least once to generate a plurality of cell populations, wherein each population is capable of producing a different component of a polyclonal protein composition; and (d) mixing the plurality of cell populations generated by steps (a)-(c) to produce a polyclonal cell population capable of producing a polyclonal protein composition.

In certain embodiments, the a cell population may be produced by transforming the population of host cells with a plurality of vectors, where each vector comprises a different copy of a nucleic acid sequence encoding more than one protein of interest that integrate into the genomic DNA of a subset of the population of host cells thereby generating a population of host cells capable of producing more than one protein of interest. In this embodiment, a polyclonal cell population and hence a polyclonal protein composition can be obtained without mixing a plurality of cell populations where each cell population produces a different component of the polyclonal protein composition.

In some embodiments, the cell population may comprise both transformed host cells and non-transformed host cells. When non-transformed host cells are present, the disclosed methods may further comprise a selection step to select the subset of transformed cells in the population. The selection step may be a negative or positive selection. Exemplary negative selection markers include, but are not limited to, G418, blasticidin, puromycin, hygromycin and zeocin. Exemplary positive selection includes the use of enzymes capable of making an essential amino acid that can be withheld from the culture media. The selection step may occur prior to mixing a plurality of individual cell populations. Alternatively, the selection step may occur after the mixing of a plurality of individual cell populations. Selection may also be performed on cell populations generated using a plurality of vectors in a single round of transformation (e.g., where each vector in the single round of transformation encodes more than one protein of interest).

Exemplary vectors that may be used in the disclosed methods include retroviral vectors, AAV vectors including AAV vectors that are single stranded DNA viral vectors, AAV vectors that are double-stranded DNA vectors and double-stranded DNA vectors that lack the genetic elements for recombinase or integrase mediated insertion into the genome of a host cell.

In exemplary embodiments, a recombinant polyclonal cell population can be generated using a retroviral integrase, or alternatively, a rep protein (or rep-like protein) from a single-stranded DNA virus. The use of a retroviral integrase protein or a viral rep protein (e.g., an adenoviral rep protein) offers advantages over other transformation methods because each are capable of mediating high efficiency and/or high efficiency preferential integration into a host cell genome (e.g., into a host cell genomic DNA). In the case of retroviral integrase protein, multiple copies of a nucleic acid of interest can be integrated into the host cell genome at locations associated with high expression. In the case of rep protein, when a human cell line is used, integration of a nucleic acid of interest typically occurs at AAVS sites. For example, a human cell line, e.g., HEK 293 cells, may be repetitively transformed to obtain cell lines containing DNA stably integrated in multiple AAVS sites, which are capable of high levels of expression. In addition, host cells may be repetitively transformed with either vector to generate a cell population that is completely transformed (e.g., at least 98% of the cells carry at least one copy of the DNA of interest). Thus, the use of a retroviral integrase, or alternatively, a rep protein from a single-stranded DNA virus, can generate large populations of individual transfected cells.

In some embodiments, the vector is a library of vectors. In some embodiments, the library of vectors encodes a plurality of polypeptides that together form a single multimeric protein.

In one aspect, the invention provides a method for producing a polyclonal cell population. The method comprises the steps of: (a) transforming one or more host cells with at least one retroviral vector comprising at least one copy of a nucleic acid sequence encoding a component of a polyclonal protein composition using a retroviral integrase protein; (b) generating a cell population capable of producing the component of the polyclonal protein composition; (c) repeating the transformation and generation steps at least once to generate a cell population capable of producing a different component of the polyclonal protein composition; and (d) mixing at least two cell populations produced by steps (a)-(c) to produce a polyclonal population of cells capable of producing the polyclonal protein composition. In the transformation step (step (a)), the at least one retroviral vector is bound or can be bound by the retroviral integrase protein. Further, transformation of the one or more host cells does not require clonal selection of an individual progenitor cell clone and/or the production of a cell line.

In some embodiments, the cell population generated in step (b) comprises transformed host cells and non-transformed host cells. In some embodiments, the method further comprises, after step (b), selecting the cell population of transformed host cells. In some embodiments, the selection step does not require selection of an individual progenitor cell or production of a call line from a single progenitor cell. In some embodiments, the selection step uses at least one selectable marker selected from the group consisting of G418, blasticidin, puromycin, hygromycin, and zeocin.

As disclosed herein, integration of a retroviral vector into a host cell genome is mediated by an integrase, which enhances the efficiency of integration. Use of a retroviral integrase protein allows for the transformation of a smaller number of cells where nearly every cell has at least one integration event. Exemplary integrases include, without limitation, integrases from RNA viruses including lentiviruses. In some embodiments, the retroviral integrase protein is selected from the group consisting of an integrase protein that is provided to the host cell in a packaging cell line, an integrase protein that is provided to the host cell encoded on another DNA vector, and an integrase protein that is provided to the host cell as a recombinant protein.

In some embodiments, transformation of one or more host cells with at least one retroviral vector comprising at least one copy of a nucleic acid sequence encoding a component of a polyclonal protein composition leads to integration of the copy of the nucleic acid sequence encoding the component of the polyclonal protein composition into the genome of the host cell.

In some embodiments, the at least one retroviral vector is a library of retroviral vectors. The library of retroviral vectors may encode a plurality of polypeptides that together form a multimeric protein. Exemplary multimeric proteins include an antibody and a T cell receptor. In other embodiments, the retroviral vector may comprise a nucleic acid encoding more than one polypeptide (e.g., the nucleic acid may encode both the immunoglobulin heavy and light chain or the nucleic acid may encode both chains of a T cell receptor).

In another aspect, the invention provides a method for producing a polyclonal cell population using a single-stranded DNA viral vector or a double-stranded DNA vector for the transformation step. The method comprises the steps of: (a) transforming one or more host cells with at least one vector comprising at least one copy of a nucleic acid sequence encoding a component of a polyclonal protein composition using a rep protein (or a rep-like protein); (b) generating a cell population capable of producing the component of the polyclonal protein composition; (c) repeating the transformation and generation steps at least once to generate a cell population capable of producing a different component of the polyclonal protein composition; and (d) mixing at least two cell populations produced by steps (a)-(c) to produce a polyclonal population of cells capable of producing the polyclonal protein composition. In the transformation step, the rep (or rep-like) protein mediates integration of the nucleic acid sequence into the host cell genome. Further, transformation of the one or more host cells does not require clonal selection of an individual progenitor cell clone and/or the production of a cell line.

In some embodiments, the cell population generated in step (b) comprises transformed host cells and non-transformed host cells. In some embodiments, the method further comprises, after step (b), selecting the cell population of transformed host cells. In some embodiments, the selection step does not require selection of an individual progenitor cell or production of a call line from a single progenitor cell. In some embodiments, the selection step uses at least one selectable marker selected from the group consisting of G418, blasticidin, puromycin, hygromycin, and zeocin.

In some embodiments, the rep protein or rep-like protein is selected from the group consisting of a rep or rep-like protein provided to the host cell in a packaging cell line, a rep or rep-like protein that is provided to the cell encoded on another DNA vector, and a rep or rep-like protein that is provided to the cell as a recombinant protein.

The single-stranded DNA viral vector or double-stranded DNA vector may be an adeno-associated viral (AAV) vector. In some embodiments, the at least one vector is a library of single-stranded DNA viral vectors or double-stranded DNA vectors (e.g., a library of AAV vectors). The library of vectors may encode a plurality of polypeptides that together form a multimeric protein. Exemplary multimeric proteins include an antibody and a T cell receptor. In some embodiments, the plurality of polypeptides comprise a polypeptide comprising an immunoglobulin heavy chain variable region and a polypeptide comprising an immunoglobulin light chain variable region that together bind a specific antigenic epitope. In other embodiments, the single-stranded DNA viral vector may comprise a nucleic acid encoding more than one polypeptide (e.g., the nucleic acid may encode both the immunoglobulin heavy and light chain or the nucleic acid may encode both chains of a T cell receptor).

In some embodiments, the plurality of polypeptides comprise two polypeptides that together form a T cell receptor (TCR). In some embodiments, the two polypeptides that together form a TCR comprise a polypeptide comprising an alpha chain of a TCR and a polypeptide comprising a beta chain of a TCR. In some embodiments, the two polypeptides that together form a TCR comprise a polypeptide comprising a gamma chain of a TCR and a polypeptide comprising a delta chain of a TCR. In some embodiments, the at least one vector comprises a nucleic acid encoding both an immunoglobulin heavy chain variable region and an immunoglobulin light chain variable region that together bind a specific antigenic epitope.

In some embodiments, the at least one vector encodes a component of a vaccine.

In some embodiments, in step (d), large populations of cells generated in step (c) are mixed to generate the polyclonal cell population. In some embodiments, the polyclonal cell population produced in step (d) comprises at least ten thousand cells. In some embodiments, the polyclonal cell population produced in step (d) comprises at least a hundred thousand cells. In some embodiments, the polyclonal cell population produced in step (d) comprises at least one million cells. In some embodiments, the polyclonal cell population produced in step (d) comprises at least 10 million cells.

In another aspect, provided herein is a method for producing a polyclonal cell population using a single-strand RNA, single-strand DNA or a double-strand DNA vector for the transformation step without genetic elements recognizable by a recombinase or integrase (e.g., a vector that does not include genetic elements recognizable by a recombinase or an integrase, e.g., a vector that is not suitable for preferential integration). An exemplary vector is shown in FIG. 14. In this aspect, since there are no genetic elements for preferential integration into the host cell genomic DNA, the integration is "random" into the host cell genomic DNA. Although random integration using the disclosed vector may result in lower numbers of transformed cells and lower overall expression levels, stable populations may be obtained. The generation of stable populations was unexpected because cells transformed by random integration are generally considered unstable.

In each of the foregoing embodiments, the one or more host cells may be transformed using multiple, repetitive transductions with the same viral vector, e.g., the host cells are transformed with the at least one viral vector at least 2, 3, 4, 5, 6, 7, 8, 9, 10 or more times. The use of multiple, repetitive transformation on the host cell population may increase the percentage of cells containing at least one copy of the viral vector integrated into the host cell genome.

In each of the foregoing embodiments, a recombinant cell population as disclosed herein may comprises at least two different cell populations where each cell is capable of producing a different recombinant protein. In an exemplary embodiment, a recombinant cell population comprises at least 2, 3, 4, 5, 6, 7, 8, 9, 10, 15, 20, 25, 50 or more cell populations with each cell population producing a different protein. In certain embodiments, where the host cell population was transformed with a plurality of vectors, the population of host cells may be capable of producing at least 2, 3, 4, 5, 6, 7, 8, 9, 10, 15, 20, or more different proteins. The recombinant protein may be an antibody, a T-cell receptor, or an agent for inclusion in a vaccine.

In some embodiments, a recombinant cell population may comprise at least two different cell populations where each cell population is capable of producing an antibody. In an exemplary embodiment, the recombinant cell population may comprise at least 2, 3, 4, 5, 6, 7, 8, 9, 10, 15, 20, or more cell populations with each cell population producing a different antibody. In an exemplary polyclonal antibody composition, the two or more antibodies may bind to the same, similar, or different antigenic epitopes, or a combination thereof. When the antibodies bind to different antigenic epitopes, the epitopes may be on one or more target polypeptides. In some embodiments, one or more of the antibodies in the recombinant antibody composition may be an antigen-binding fragment.

In some embodiments, a recombinant cell population may comprise at least two different cell populations where each cell population is capable of producing a different recombinant protein to be included in a vaccine. In an exemplary embodiment, the recombinant cell population may comprise at least 2, 3, 4, 5, 6, 7, 8, 9, 10, 15, 20, or more cell populations with each cell population producing a different recombinant protein for inclusion into a vaccine. The recombinant proteins, for example, may resemble one or more infectious agents of the same pathogen, variants of a given infectious agent (e.g., mutant forms), or different infectious agents.

In some embodiments, a recombinant cell population may comprise at least two different cell populations where each cell population is capable of producing an T cell receptor. In an exemplary embodiment, the recombinant cell population may comprise at least 2, 3, 4, 5, 6, 7, 8, 9, 10, 15, 20, or more cell populations with each cell population producing a different T cell receptor. The T cell receptor may recognizing the same, similar, or different antigens bound to a major histocompatibility complex molecule, or a combination thereof. A polyclonal T cell receptor composition may be a combination of alpha-beta heterodimers and gamma-delta heterodimers.

The at least two individual cell populations may be mixed at a 1:1 ratio or ratios different from 1:1 to generate a recombinant polyclonal cell population. In an exemplary embodiment, the recombinant polyclonal cell population may comprise at least 100 cells, at least 1,000 cells, at least 10,000 cells, at least 100,000 cells, at least 1 million cells, at least 10 million cells, at least 20 million cells, or more. In an exemplary embodiment, each individual cell population is equally represented in the polyclonal cell population.

A recombinant cell population may be banked for further use including future testing, screening, manufacturing, or use (e.g., therapeutic polyclonal antibodies, vaccine production, etc.). In exemplary embodiments, individual cells lines are not banked prior to generation of a recombinant polyclonal cell population.

In some embodiments, the methods comprise purifying a polyclonal protein composition from a polyclonal cell population. In some embodiments, the polyclonal protein composition is purified by a method selected from the group consisting of: gel filtration, affinity chromatography, ion exchange chromatography, and hydrophobic interaction chromatography. In some embodiments, the stability of the polyclonal protein composition is determined by a method selected from the group consisting of: ion exchange chromatography, HPLC, papain digestion followed by 2-D gel analysis, microarray, qPCR, and an ELISA assay.

In another aspect, the present disclosure provides cell population produced by the methods described herein.

In a further aspect, the present disclosure provides a recombinant antibody composition produced by the methods described herein.

These and other aspects and advantages of the invention are illustrated by the following figures, detailed description and claims. As used herein, "including" means without limitation, and examples cited are non-limiting.

DETAILED DESCRIPTION

Figure 1:
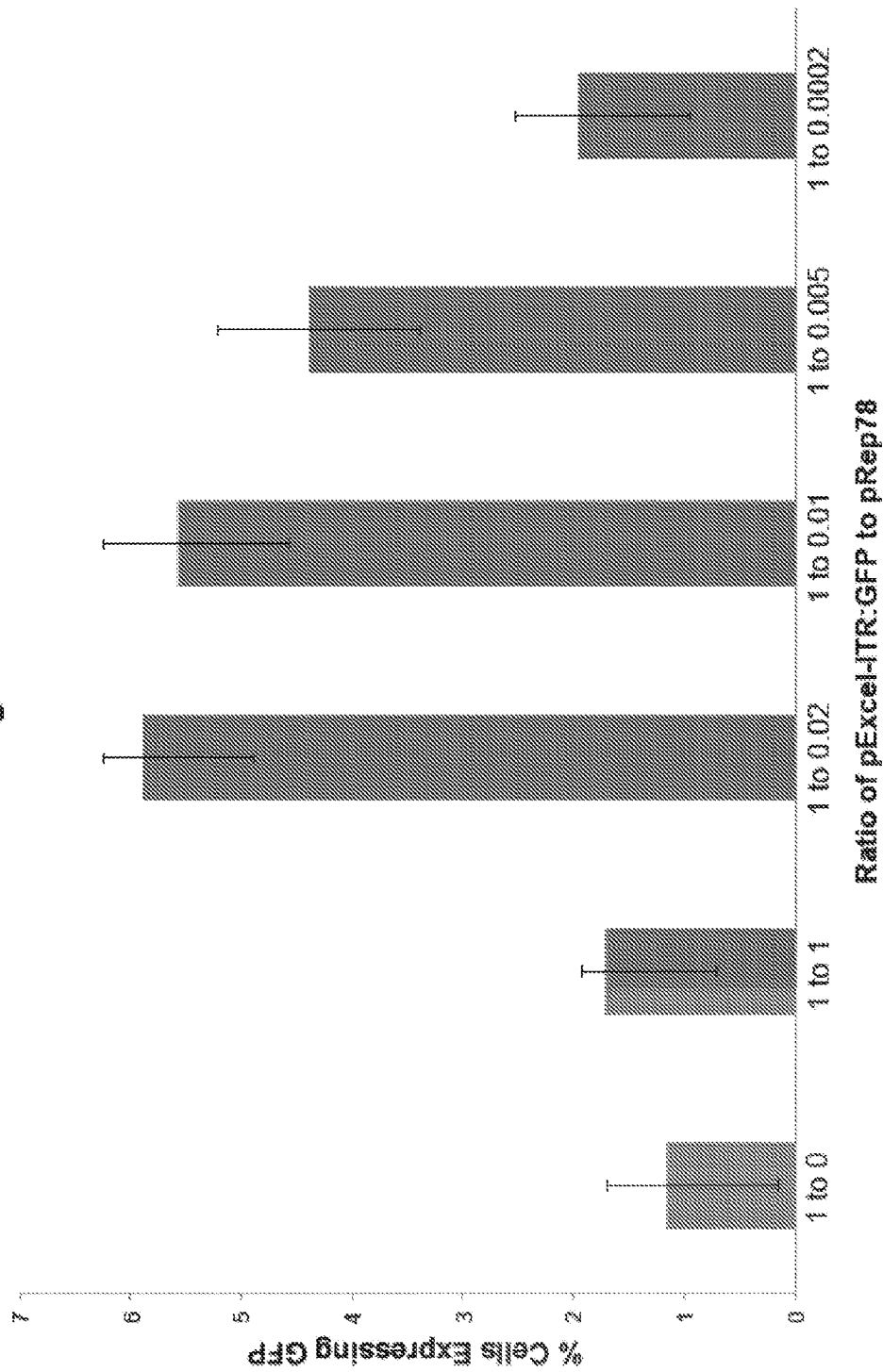
FIG. 1 is a graph showing that AAV Rep protein enhances stable expression of exogenous DNA sequences in cultured cells.

Disclosed herein are methods for producing stable cell populations (e.g., cell populations expressing a single recombinant polypeptide and cell populations expressing multiple recombinant polypeptides) and methods for producing recombinant polyclonal proteins such as antibodies, T cell receptors, and vaccines. The disclosed methods offer a significant advantage over known methods for producing stable cell populations and/or methods for producing recombinant polyclonal proteins because the disclosed methods do not require clonal selection (i.e., the use of a selection marker to select an individual cell clone—the progenitor cell—that is then propagated as an individual cell line). As a result, the disclosed methods are faster and more efficient than methods requiring the selection of individual stable cell clones.

As described herein, stable cell populations expressing either a single recombinant polypeptide or multiple recombinant polypeptides can be generated from large populations of individual transformed cells, which offer a surprising advantage for preparing and maintaining stable cell populations. Moreover, it was unexpected that cell populations generated using the disclosed methods could be maintained without a bias to certain cells in the population over time. In addition, because large populations of cells are used to generate stable cell populations (referred to herein as a "recombinant polyclonal cell population" or a "polyclonal cell population"), the disclosed methods do not require banking of individual cells lines (e.g., individual clonal cell lines generated from a single progenitor cell using a selection process).

The recombinant cell populations (e.g., cell populations expressing a single recombinant polypeptide and cell populations expressing multiple recombinant polypeptides) described herein behave within certain mathematical limits as outlined in the evolutionary dynamics of large, but finite populations (see, e.g., M. Smith, (1974) J. Theor. Biol. 47:209-221, which describes initial models defining criteria where mutants would be evolutionarily less fit in order to maintain a evolutionary stable population; Crawford (1990) J. Theor. Biol. 145:83-94, which describes that by using the Nash equilibrium it was feasible to mathematically determine that a finite, but large populations could remain stable; Nowak et al. (2004) Nature 428:646-650 and Lessard (2005) Theor. Population Biol. 68: 19-27, which demonstrated that mutation deviations can take over a population only if they exceed certain threshold values that increase with increasing population size). According to these models, there is a high probability that when finite, but large populations of a similar type are mixed together, they remain stable over a limited length of time; however, the length of time may in essence be infinite in the context of sufficiently large populations.

Without wishing to be bound by theory, the model of stable evolutionary behavior can be applied to recombinant cell populations (e.g., cell populations expressing a single recombinant polypeptide and cell populations expressing multiple recombinant polypeptides) by starting with large individual transformed cell populations. For a polyclonal cell population, each individual cell population may be related based on the practical applications for expression of recombinant polyclonal proteins with similar profiles for growth and protein expression. It is contemplated herein that the ratios of each of the component cell populations can be adjusted as desired to obtain a mixture of cell populations each expressing a single protein and as a whole expressing a defined stable mixture of multiple proteins in whatever ratio desired. For example, if the recombinant polyclonal cell population is a cell population for producing a recombinant polyclonal antibody, the ratio of each individual cell population each producing a single antibody can be adjusted to produce a therapeutically effective polyclonal antibody population taking into account the role of each individual antibody in the polyclonal mixture.

The disclosed methods are designed to achieve balance in the polyclonal cell populations. For example, balance is required both when making a multi-component protein, such as an antibody, and in mixed cell populations containing different antibodies. Balance in a polyclonal cell population can be achieved by generating individual cell populations that are stable and then mixing the stable individual cell populations to obtain a polyclonal cell population. To achieve stability in both the individual cell population and the polyclonal cell population, the evolutionary dynamics of both populations must be considered. As disclosed herein it was surprisingly discovered that when large populations of similar cells are mixed together they remain stable over a limited length of time without bias to certain cells in the population over time; however, the length of time may in essence be infinite in the context of sufficiently large populations.

Stable polyclonal cell populations can be consistently generated as described herein when sufficient numbers of individual cells are used to produce a cell population. It is contemplated herein that when cell populations with greater than 10,000 individual cells are mixed, the combined cell population yields a stable polyclonal cell population to produce such a polyclonal protein product for a limited length of time that in the process of production of that polyclonal protein is essentially infinite.

In exemplary embodiments, the stable cell populations described herein are obtained by transforming a population of host cells using preferential integration of at least one vector comprising at least one copy of a nucleic acid sequence encoding a protein of interest into the host cell genomic DNA to generate large populations of individual transformed cells. The disclosed methods using preferential integration can be used to produce cell populations expressing a single recombinant polypeptide and multiple recombinant polypeptides. Exemplary vectors for preferential integration are described in greater detail below.

Before further description of the disclosed methods, certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

The term "cell line" as used herein refers to a population of cells derived from a single progenitor cell. Persons skilled in the art would understand that because cells contained in a given cell line are derived from a single progenitor cell that each of the cells in the cell line, at least initially, share the same genomic characteristics (see, e.g., Poste et al., PNAS 1981 78:6226-6230). A cell line is typically generated by selecting for an individual progenitor cell clone (e.g., using a selection marker, e.g., an antibiotic selection marker, e.g., neomycin, blasticidin, puromycin, or hygromycin). The individual progenitor cell clone is then cultured to expand the cell line capable of producing a gene product of interest.

The terms "cell population", "cell mixture", "transformed cell population" and "recombinant cell population" as used herein refer to a population of cells that share a common genetic background, but are not genetically identical. In a cell population expressing a single recombinant polypeptide, a DNA fragment of interest is integrated into a plurality of cells, where the integration site in each cell may be at one or more locations in the genome, creating cells in the population that are not genetically identical. A cell population differs from a cell line because the cell population is not derived from an individual protein cell and/or is not comprised of cells with the same genetic content. For example, in the cell populations described herein there is no selection process to identify a single progenitor cell followed by clonal expansion of the single progenitor cell. Rather the cell populations described herein are a mixture of cells where each cell in the mixture may have the DNA integrated in one or more locations in the genome. Stability of the cell population expressing a single recombinant polypeptide is achieved by population dynamics.

In exemplary embodiments, the cell population, cell mixture or transformed cell populations described herein may be a polyclonal, e.g., it expresses multiple recombinant polypeptides. In a polyclonal cell population more than one DNA fragment of interest is integrated into a plurality of cells, wherein the integration site in each cell may be at one or more locations in the genome, creating cells that are not genetically identical. A polyclonal cell population as described herein may be generated by mixing two or more monoclonal cell populations. Alternatively, a polyclonal cell population maybe generated by a bulk transformation procedure wherein a plurality of DNA fragments of interest is integrated into a plurality of host cells (e.g., one DNA fragment of interest per host cell). A polyclonal cell population as described herein does not require a selection process to identify individual progenitor cells followed by clonal expansion of individual cell lines (e.g., a polyclonal cell population is not a mixture of individual cell lines each derived from an individual progenitor cell). Stability of the polyclonal cell population is achieved by population dynamics.

The term "transformation" as used herein refers to any method for introducing foreign DNA into a cell. As used herein, "transformation" is a broad term that includes methods for introducing foreign DNA into a cell including transfection, infection, transduction or fusion of a donor cell and an acceptor cell.

The term "random integration" as used herein refers to the process of integrating a DNA fragment of interest (e.g., a partial or complete DNA encoding a protein of interest) into the genome of a cell, where the fragment of DNA can be integrated in any part of that genome with equal probability. The person skilled in the art would understand that random integration refers to a transformation procedure where nothing is done to guide the expression construct to a predetermined position in a host cell genome. For example, in certain embodiments, random integration refers to an integration process which is performed naturally by the host cell machinery without the aid of extraneously added sequences or enzymes that affect the natural integration site (H. Würtetle, Gene Therapy, 2003, 10:1791-1799).

The term "site-specific integration" as used herein refers to the process of integrating a DNA fragment of interest (e.g., a partial or complete DNA encoding a protein of interest) into the genome of a cell, where the DNA fragment of interest is targeted to a specific sequence in that genome. The specific target sequence can occur naturally in the genome or may be engineered into the genome of the host cell (e.g., engineering of a FRT-site into the genome of a cell for Flp recombinase mediated integration).

An example of site-specific integration is the use of Flp recombinase to target integration of a DNA fragment of interest to a specific site in a host cell genome. The specific site of integration occurs at a DNA sequence known as the FRT site. FLP is an exception among integrases in that it is highly specific to FRT sites. Site specific integration of DNA to the FRT site can be achieved by including FRT site DNA sequence in the DNA fragment for targeted integration. However, since FRT sites do not occur naturally in most genomes, typically, a FRT site must be integrated into the genome of a host cell of interest before introduction of the DNA fragment of interest.

The term "preferential integration" as used herein refers to the process of integrating a DNA fragment of interest (e.g., a partial or complete DNA encoding a protein of interest) into the genome of a cell, where the fragment of DNA is targeted to a predetermined region of the genome (but not to a single defined site, e.g., a FRT site). As described herein, preferential integration is not a random integration event because there is an increased probability that the DNA of interest will integrate into a defined region or specific site in the host cell genome. Preferential integration also differs from the site-specific integration because there is variability in the integration site.

Examples of preferential integration include integration using an AAV system by the AAV rep protein(s). Stable integration into the AAVS1 site is mediated by inverted terminal repeat or "ITR" sequences, where each ITR sequence comprise 145 base pairs (see, e.g., Bohenzky et al., (1988) Virology 166 (2): 316-27; Wang, X S et al., (1995) J. Mol. Biol. 250(5):573-80; Weitzman, M D et al., (1994) PNAS 91(13):5808-12). Recent data suggests the AAV vector integrates into the host cell into a rep targeting sequence ("RTS") such as an AAVS1 site located on chromosome 19 with an efficiency of ~10%, with the remaining 90% spread over other RTS sites across the human genome (as described in e.g., Smith R H, Gene Therapy (2008) 15, 817-822 and Hüser et al., PLoS Pathog 6(7): e1000985. doi:10.1371/journal.ppat.1000985).

Other examples of preferential integration include use of a retroviral vector system, wherein the retroviral vector integrates into open chromatin domains which encompass about 5% of the total genome; use of a phage integrase ΦC31 or lambda integrase, which carries out recombination between the attP site and the attB site (A. C. Groth et al., PNAS, 2000, 97:59995-6000); and use of a Cre recombinase and a variety of lox sites such as loxP from bacteriophage P1 or variants or mutants thereof, e.g., lox43, lox 44, lox 66, lox71, lox 75, lox 76, and lox 511 (C. Gorman and C. Bullock, Curr. Opinion in Biotechnology 2000:11:455-460). Differences in preferential integration may also be observed with certain retroviral integrases, e.g., HIV integrates preferably into chromosomal regions rich in expressed genes, MMLV integrates preferably near transcription start sites, and ASLV which integrates with weak preference for active genes, but no preference for transcription start regions (Mitchell et al., PLoS Biol, 2004, 2:e234).

I. Expression Vectors

Expression vectors of the invention are constructed to encode at least one polypeptide of interest. As used herein, the terms "polypeptide of interest" and "protein of interest" refer to a protein encoded by a nucleic acid or gene of interest. It is contemplated herein that the disclosed methods are not limited by the type of polypeptides or protein that may be expressed by the recombinant polyclonal cell populations. Exemplary proteins of interest include antibodies (comprising immunoglobulin heavy chains and immunoglobulin light chains) or fragments thereof, T cell receptor molecules, and protein components of a vaccine.

As used herein, the term "component of a polyclonal protein composition" refers to a protein included in the polyclonal protein composition. The protein may comprise a single polypeptide or it may be a multimeric protein comprising two or more polypeptide chains. Exemplary multimeric proteins include antibodies and T cell receptors. For example, an intact, tetrameric antibody is produced from two different polypeptide sequences referred to as the immunoglobulin heavy chain and the immunoglobulin light chain that together bind to a specific target polypeptide. A T cell receptor (TCR) is a heterodimeric protein comprising two polypeptide chains (e.g., the heterodimer may contain alpha and beta polypeptide chains or gamma and delta polypeptide chains).

When the component of a polyclonal protein composition comprises a single polypeptide, the protein component can be encoded by a single expression vector. For example, the expression vector may contain at least one copy of a nucleic acid sequence that encodes the single polypeptide of interest.

It is also contemplated that a single expression vector may contain a nucleic acid encoding for more than one polypeptide. For example, a single expression vector may contain at least one copy of a nucleic acid sequence encoding both the immunoglobulin heavy and light chain sequences or a nucleic acid sequence encoding both polypeptide chains of a TCR. When the expression vector comprises more than one nucleic acid of interest (e.g., both an immunoglobulin heavy chain and an immunoglobulin light chain or both chains of a TCR), the nucleic acids of interest may be arranged in the vector in a polycistronic sequence, and may, optionally, be separated by an internal ribosome entry site (IRES). Alternatively, each nucleic acid of interest may be arranged in the vector under the control of individual regulatory elements (e.g., promoter and/or enhancer sequences). In some embodiments, each nucleic acid of interest may be arranged in the vector in the same orientation, but under the control of individual regulatory elements. In other embodiments, each nucleic acid of interest may be arranged in the vector in opposite orientations.

Alternatively, a component of a polyclonal protein composition may be encoded by more than one expression vector. For example, when the component of the polyclonal composition is a multimeric protein, the two or more polypeptides may be encoded on at least two different expression vectors (e.g., an immunoglobulin heavy chain and light chain are encoded on separate vectors). Accordingly, when the individual polypeptide chains of a multimeric protein are contained on more than one vector, the skilled person would understand that both vectors are transfected into the same host cell to produce the multimeric protein.

In an exemplary embodiment, a library of vectors may be used to encode a plurality of polypeptides that together form a single multimeric protein (e.g., an antibody or a TCR). For example, the library of vectors may comprise a plurality of vectors where each vector contains a nucleic acid encoding one or more polypeptides. The skilled person would understand that the library of vectors can be transfected into a single host cell to produce a multimeric protein.

Exemplary expression vectors include viral vectors capable of integration into a host cell genome such as a retroviral vector and a single-stranded DNA viral vector (e.g., an adenoviral vector).

Exemplary retroviral vectors (also known as retrovectors) may be derived from retroviruses, e.g., Moloney Murine Leukemia Virus (MoMuLV) and the Rous Sarcoma Virus (RSV), and lentiviruses that are capable of integrating into the genome of a host cell. Retroviruses are capable of introducing DNA fragments into cells and integrating them into the genome through the activity of a virus-encoded integrase enzyme. Integrase-mediated proviral integration is highly efficient compared with random integration or recombinase-based methods. Retroviral integration occurs preferentially in areas of open chromatin, which leads to lower rates of expression silencing compared with other methods. Retroviral integration can occur at a single site or at multiple sites throughout the genome, and copy number can be increased through multiple rounds of transduction or higher multiplicity of infection (discussed in greater detail below).

A variety of retroviral vectors are well-known in the art. In some embodiments, the retroviral vector may be replication-defective (e.g., essential genes for viral replication, e.g., genes encoding virion structural, replicatory and DNA modifying proteins, are deleted or disabled). The skilled person understands that deletion of such genes can provide space in the vector for the insertion of a DNA of interest (e.g., 8-10 kb DNA fragments). The virion structural, replicatory, and DNA modifying proteins are provided in trans during viral packaging in a packaging cell line, through transient co-transfection of nucleic acids encoding the virion proteins (e.g., the integrase protein is encoded on another DNA vector), or as a recombinant protein. Using this method, it is possible to achieve high viral titers. By infecting a cell population repeatedly with retroviruses packaged in this way, multiple genomic insertions can be achieved, leading to stable, high-level expression of a recombinant protein of interest. This is in contrast to the instability characteristic of cell lines created through transfection and integration of multiple copies of plasmid encoded cDNAs or through gene amplification methods.

In general, the retroviral vector includes one or more genes of interest flanked by "long terminal repeat" or "LTR" sequences (i.e., the 5' and 3' LTRs). It is contemplated that a retroviral vector of the invention is not limited to a specific LTR. Exemplary LTRs include, but are not limited to, MoMLV, MoMuSV, MMTV, HIV, and equine infectious anemia LTRs. The LTRs may contain sequences required for the association of viral genomic RNA, reverse transcriptase and integrase functions, and sequences involved in directing the expression of the genomic RNA to be packaged in viral particles. Exemplary retroviral vectors are disclosed in U.S. Pat. Nos. 6,852,510, and 7,378,273, which are incorporated herein by reference.

In some embodiments, the retroviral vector may be a pseudotyped retroviral vector comprising a G glycoprotein (e.g., the G glycoprotein may be selected from the group consisting of vesicular stomatitis virus, Piry virus, Chandipura virus, Spring viremia of carp virus, and Mokola virus G glycoproteins).

Other viral vectors and transduction methods also have been described, including lentivirus systems (e.g., human immunodeficiency virus 1 and 2 (HIV-1 and HIV-2), simian immunodeficiency virus (SIV), feline immunodeficiency virus (FIV), equine infectious anemia virus (EIAV), caprine arthritis encephalitis virus (CAEV), visna virus, and Jembrana disease virus (JDV)). Lentiviral vectors and systems are of interest because of their ability to infect non-dividing, terminally differentiated cells and to insert into the genome though an integrase-based mechanism. Although HIV-based systems raise some safety concerns related to the production of human clinical products and gene therapy applications, a number of related animal viruses are being developed for these purposes (see, e.g., Olsen, J. C. (1998) Gene Therapy 5:1481-1487). Additionally, further elements not commonly found on retroviral virons, such as introns may be incorporated using methods known in the art (Blø et al., DNA Cell Biol. 2007, 26:773-9).

Alternatively, retroviral elements may be used without creating virus particles on DNA plasmids. These DNA plasmids are similar in concept to those described for the double stranded DNA plasmids for AAV as described above, except the AAV ITR sequences are substituted with retroviral LTRs and the rep protein is replaced with a retroviral integrase.

Alternatively, single-stranded DNA viruses may be used to integrate a nucleic acid of interest into a host cell genome. Single-stranded DNA viruses include, but are not limited to, viruses classified as group II or group VII in the Baltimore classification system of DNA viruses. Examples of group II viruses include adeno-associated virus (AAV) and parvoviruses, and an example of group VII viruses includes hepatitis B virus.

An exemplary single-stranded DNA virus is adeno-associated virus (AAV), which is capable of infecting both dividing and non-dividing cells and has the ability to stably integrate into the host cell genome at a specific site, designated as AAVS1, in human chromosome 19 approximately 10% of the time with the remaining 90% spread over other RTS sites across the human genome (Hüser et al., PLoS Pathog 6(7): e1000985. doi:10.1371/journal.ppat.1000985). Stable integration into the AAVS1 site is mediated by inverted terminal repeat or "ITR" sequences, where each ITR sequence comprise 145 base pairs (see, e.g., Bohenzky et al., (1988) Virology 166 (2): 316-27; Wang, X S et al., (1995) J. Mol. Biol. 250(5):573-80; Weitzman, M D et al., (1994) PNAS 91(13):5808-12).

The nucleotide sequences of AAV ITR regions are well-known in the art (see, e.g., Kotin (1994) Human Gene Therapy 5:793-801). Exemplary AAV ITR sequence may be wild-type nucleic acid sequences or, alternatively, they may be altered by the insertion, deletion, or substitution of one or more nucleotides. AAV ITR sequences may be derived from any AAV serotype, including without limitation, AAV-1, AAV-2, AAV-3, AAV-4, AAV-5, AAVX7. In general, 5' and 3' ITR sequences flank the selected nucleic acid of interest, however, the skilled person will understand that 5' and 3' ITR sequences may be derived from the same or different AAV serotypes.

Exemplary AAV vectors are well-known in the art and include, without limitation, AAV-1, AAV-2, AAV-3, AAV-4, AAV-5, AAVX7 (see, e.g., U.S. Pat. No. 6,852,510).

The rep protein of AAV has also been shown to be necessary for the AAVS1-specific integration of the AAV genome. The rep protein may be provided in cis (i.e., on the same vector as the nucleic acid of interest flanked by ITR sequences) or it may be provided in trans as either a recombinant protein or on another DNA vector including, without limitation, an episomal vector (see, e.g., Weitzman, M D et al., supra; Zhou & Muzyczka (1998) J. Virol. 72(4):3241-7).

Similar to retroviruses, the cloning capacity of the AAV vector results from the replacement of viral genes. Although the cloning capacity of the AAV vector is limited, 4.8 kilobases (kb), the insertion space is sufficient for expression of polypeptides (e.g., an immunoglobulin light chain is encoded by a cDNA of approximately 670 base pairs and an immunoglobulin heavy chain is encoded by a cDNA of approximately 1.2 kb) providing approximately 3.0 kb for the insertion of various regulatory and expression elements. In some embodiments, the AAV vector may be designed to include ITR sequences from more than one genome arranged (e.g., annealed) to form head-to-tail concatamers, which can double the cloning capacity of the vector.

Figure 15:
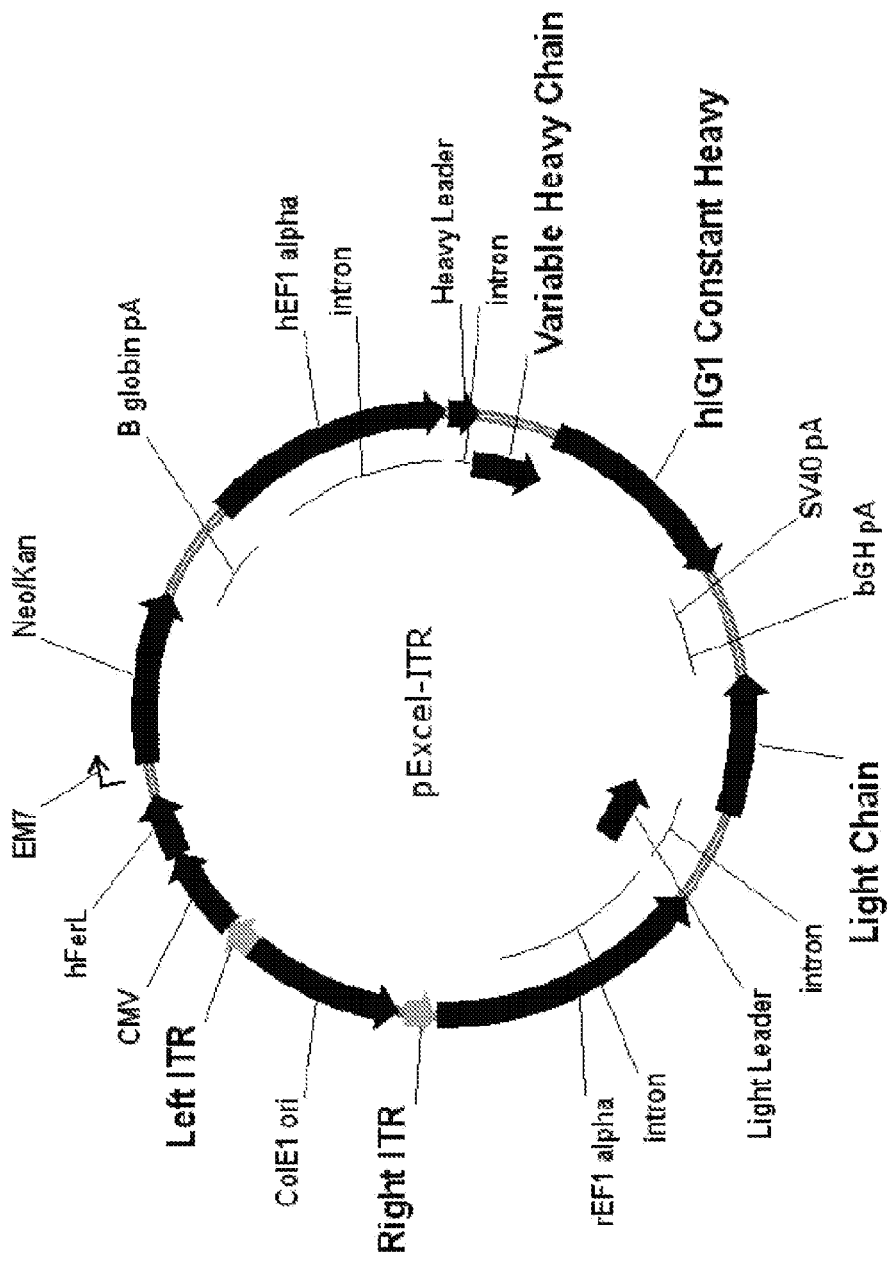
FIG. 15 is a schematic representation of a pEXCEL/ITR expression vector comprising the following elements: Left ITR and Right ITR=Inverted Terminal Repeat sequences from AAV2; ColE1 ori=bacterial origin of replication; CMV=CMV enhancer; hFerL=hFerL eukaryotic core promoter, driving expression of the resistance gene; EM7=bacterial promoter driving expression of the resistance gene; Neo/Kan: Neomycin (eukaryotic)/Kanamycin (prokaryotic) resistance gene; B globin pA=Beta globin polyadenylation sequence; hEF1 alpha=human EF1 alpha promoter; Heavy Leader=leader, for example from Vh5-51; Light Leader=leader, for example from k2-05; Variable Heavy Chain=Variable region of the heavy chain of the antibody of interest, flanked by restriction sites; hIG1 Constant Heavy=cDNA of the human IgG1 constant region; BGH pA=BGH polyadenylation sequence SV40 pA=SV40 polyadenylation sequence; Light Chain=Variable and constant regions of either lambda or kappa antibody of interest, flanked by restriction sites; and rEF1 alpha=rat EF1 alpha promoter (introns and exons are annotated for the EF1 alpha promoters and the leaders).
Figure 17:
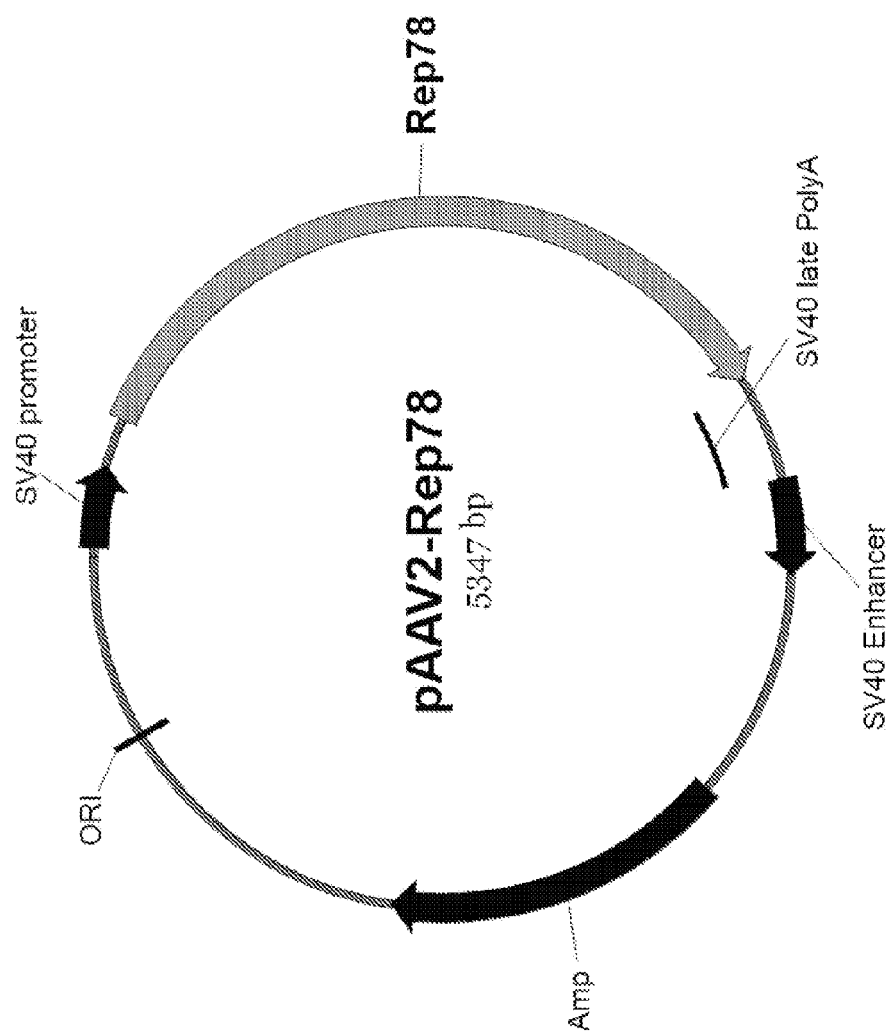
FIG. 17 is a schematic representation of a Rep78 vector, comprising the following elements: SV40 promoter=eukaryotic promoter from Rep78; Rep78=coding sequence of Rep78 from AAV2; SV40 late pA=late polyadenylation sequence from SV40; Amp=Ampicillin resistance gene and bacterial promoter; and ORI=initiation site for a bacterial origin of replication.

In certain embodiments, the size limitation embodied by having to generate virons from AAV or retroviral vectors can be circumvented by creating double stranded plasmid DNA vectors carrying respectively ITRs for AAV or LTRs for retroviral vectors and providing the integrase, be it the AAV rep protein or a retroviral integrase in trans, either on a DNA vector or as a protein. As examples, a vector map depicted in FIG. 15 shows one such ITR double stranded DNA vector and a vector map depicted in FIG. 17 shows a rep expression plasmid.

To produce a vector (e.g., a retrovector or an AAV vector) containing one or more genes of interest, e.g., DNA molecules encoding protein of interest, can be chemically synthesized using publicly available or previously determined sequence information. Synthetic DNA molecules can be ligated to other appropriate nucleotide sequences, including, e.g., constant region coding sequences, and expression control sequences, to produce conventional gene expression constructs encoding the desired protein. In some embodiments, when the protein of interest is an antibody, the antibody sequences can be cloned from B-cells, such as e.g., plasma cells or out of hybridomas by conventional hybridization techniques or polymerase chain reaction (PCR) techniques, using synthetic nucleic acid probes whose sequences are based on sequence information provided herein, or prior art sequence information regarding genes encoding the heavy and light chains of antibodies in B-cells or hybridoma cells.

Production of defined gene constructs is within routine skill in the art. Nucleic acids encoding desired antibodies can be incorporated (ligated) into expression vectors between, e.g., the 5' and 3' LTR sequences of a retroviral vector or the 5' and 3' ITR sequences of an AAV vector. The vector may also include sequences necessary for the efficient expression of the gene of interest such as promoter and/or enhancer sequences, splicing signals, and sequences required for the efficient packaging of the viral RNA into infectious virions (e.g., the packaging signal (Psi), the tRNA primer binding site (−PBS), the 3' regulatory sequences required for reverse transcription (+PBS)).

The one or more genes of interest may be operable linked to a regulatory element such as a promoter and/or enhancer. It is contemplated that the invention is not limited to a specific promoter. Suitable promoters for expressing the genes of interest include, but are not limited to, the EF1alpha promoter, CMV promoter, the beta-actin promoter, the FerL promoter, composite promoters such as the CMV EF-1 alpha combinations, the SV40 enhancer, basal promoter and tripartite leader composite promoters, the RSV LTR, and long terminal repeat of Moloney Murine Leukemia Virus. Suitable enhancers for expressing the one or more genes of interest include the SV40 and CMV enhancers.

The vector may also include splicing sequences associated with an intron, examples of such introns are beta globin intron1, EF-1 alpha intron 1 and beta actin intron 1, and/or one or more poly A sequences such as the early and late SV40 polyA, bovine growth hormone polyA, human growth hormone polyA, EF-1 alpha polyA and thymidine kinase polyA.

In some embodiments, where secretion of the protein of interest is desired, the vectors may be modified to include a signal peptide sequence. In general, signal peptide sequences may comprise about 15 to 30 hydrophobic amino acid residues. (See, e.g., Zwizinski et al., (1980) J. Biol. Chem. 255(16): 7973-77, Gray et al., Gene 39(2): 247-54 [1985], and Martial et al., (1979) Science 205: 602-607). Signal peptide sequences are known in the art and may include, but are not limited to, signal peptide sequences derived from human growth hormone, lactoferrin, tissue plasminogen activator, serum albumin alpha-casein, secreted alkaline phosphatase, antibody kappa, lambda or heavy chain germlines, and alpha-lactalbumin.

The vector may also include additional an "internal ribosome entry site" or "IRES" sequence located between polycistronic genes to permit production of expression products originating from, e.g., a second gene by internal initiation of the translation of the polycistronic mRNA. Vectors incorporating IRES sequences are known in the art.

The vector may also include additional a 2A/furin sequence located between polycistronic genes to permit production of expression products originating from e.g., a second gene by enzymatic cleavage of the protein product. Vectors incorporating 2A/furin sequences are known in the art (Jostock et al., Appl Microbiol Biotechnol (2010) 87:1517-1524).

The vector may also be modified to include an RNA export element either 5' or 3' to the gene of interest (See, e.g., U.S. Pat. Nos. 5,914,267; 6,136,597; and 5,686,120; and WO99/14310). Inclusion of an RNA export element can result in high expression of a protein of interest without incorporating splice signals or introns in the nucleic acid sequence encoding the protein of interest.

In an exemplary embodiment, the vectors of the invention do not contain a selectable marker providing for the selection of transformed cells.

As discussed above, in general, a retroviral vector may have the following structure:

LTR-XXXXX-LTR wherein, the XXXXX flanked by the LTR sequences can be combination of elements such as a promoter, a leader sequence, a nucleic acid sequence encoding a protein of interest (e.g., a light chain sequence and/or a heavy chain sequence or a T cell receptor sequence), and/or a poly A sequence. Other regulatory elements may optionally be included.

In an exemplary embodiment, a retroviral vector comprising both the immunoglobulin heavy chain and the immunoglobulin light chain may have the following structure:

LTR-X-promoter for the light chain-kappa leader
sequence-immunoglobulin light chain sequence-
poly A sequence for the light chain-enhancer
for the heavy chain-promoter for the heavy
chain-heavy chain leader sequence-immuno-
globulin heavy chain variable sequence-heavy
chain constant region sequence (CH)-poly A
sequence for the heavy chain-X-LTR.

Retroviral vectors having this structure contain both the immunoglobulin heavy chain and light chain sequence in the same orientation. Exemplary promoters for this retroviral vector include the EF1alpha promoter with a CMV enhancer and/or a SV40 enhancer preceding the promoter. In some embodiments, the retroviral vector may include a combination of regulatory elements, for example, a human EF-1 alpha promoter with a CMV enhancer before a light chain sequence, and a rat or mouse EF-1 alpha promoter with a SV40 enhancer before a heavy chain sequence. In certain embodiments, a combination of regulatory elements such as a human EF-1 alpha promoter driving expression of one nucleic acid and a rat or mouse EF-1 alpha promoter driving the expression of a second nucleic acid may enhance the stability of the retroviral vector construct.

In another embodiment, a retroviral vector comprising both the immunoglobulin heavy chain and the immunoglobulin light chain may have the following structure:

LTR-X-poly A for the light chain-light chain
  sequence-kappa leader sequence-promoter for
  the light chain-enhancer sequence-promoter for
  the heavy chain-heavy chain leader sequence-
  immunoglobulin heavy chain variable sequence-
  heavy chain constant region sequence (CH)-
  poly A sequence for the heavy chain-X-LTR.

Retroviral vectors having this structure contain both the immunoglobulin heavy chain and light chain sequence in the opposite orientation. Exemplary promoters for this vector include the EF-1 alpha promoter with a CMV enhancer and/or a SV40 enhancer preceding the promoter, or a combination of regulatory elements.

In another exemplary embodiment, a retroviral vector comprising only the immunoglobulin light chain may have the following structure:

LTR-X-promoter for the light chain-kappa leader
  sequence-immunoglobulin light chain sequence-
  poly A sequence for the light chain-X-LTR.

Exemplary promoters for this retroviral vector include the EF-1alpha promoter with a CMV enhancer and/or a SV40 enhancer preceding the promoter, or a combination of regulatory elements.

In another exemplary embodiment, a retroviral vector comprising only the immunoglobulin heavy chain may have the following structure:

LTR-X-promoter for the heavy chain-heavy chain
  leader sequence-immunoglobulin heavy chain
  variable sequence-heavy chain constant region
  sequence (CH)-poly A sequence for the heavy
  chain-X-LTR.

Exemplary promoters for this retroviral vector include the EF-1alpha promoter with a CMV enhancer and/or a SV40 enhancer preceding the promoter, or a combination of regulatory elements.

Exemplary AAV vectors may have a structure similar to those described above, except that the flanking LTR sequences are replaced by flanking ITR sequences.

Figure 14:
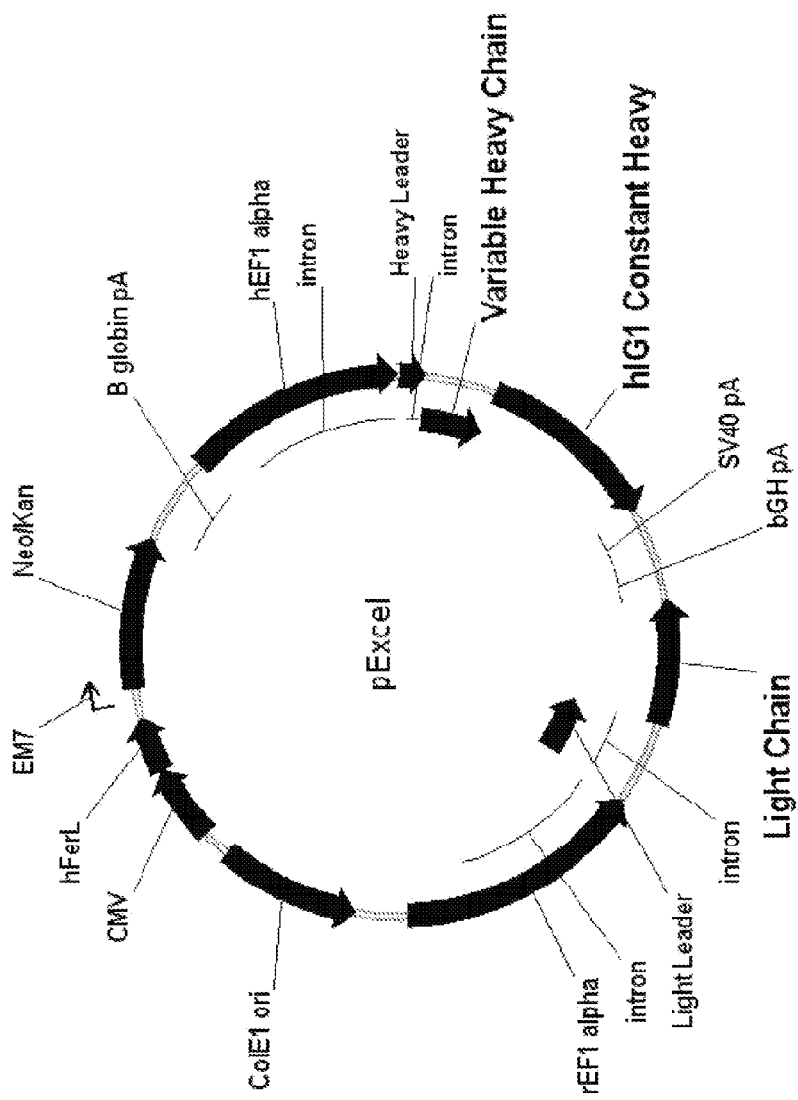
FIG. 14 is a schematic representation of a pExcel antibody expression vector comprising the following elements: ColE1 ori=bacterial origin of replication; CMV=CMV enhancer; hFerL=hFerL eukaryotic core promoter, driving expression of the resistance gene; EM7=bacterial promoter driving expression of the resistance gene; Neo/Kan: Neomycin (eukaryotic)/Kanamycin (prokaryotic) resistance gene; B globin pA=Beta globin polyadenylation sequence; hEF1 alpha=human EF1 alpha promoter; Heavy Leader=leader, for example from VhX; Light Leader=leader, for example from kX; Variable Heavy Chain=Variable region of the heavy chain of the antibody of interest, flanked by restriction sites; hIG1 Constant Heavy=cDNA of the human IgG1 constant region; SV40 pA=SV40 polyadenylation sequence; BGH pA=BGH polyadenylation sequence; Light Chain=Variable and constant regions of either lambda or kappa antibody of interest, flanked by restriction sites; and rEF1 alpha=rat EF1 alpha promoter (introns and exons are annotated for the EF1 alpha promoters and the leaders).

FIG. 14 shows a diagram of an exemplary antibody expression vector referred to herein as pExcel. The pExcel vector can be used to express both the heavy chain and light chain of an immunoglobulin for transient expression or integration of the antibody expression cassettes to generate a polyclonal cell population as described herein. The pExcel vector for both heavy chain and light chain immunoglobulin expression contains the following elements: ColE1 ori=bacterial origin of replication; CMV=CMV enhancer; hFerL=hFerL eukaryotic core promoter, driving expression of the resistance gene; EM7=bacterial promoter driving expression of the resistance gene; Neo/Kan: Neomycin (eukaryotic)/Kanamycin (prokaryotic) resistance gene; B globin pA=Beta globin polyadenylation sequence; hEF1 alpha=human EF1 alpha promoter; Heavy Leader=leader, for example from VhX; Light Leader=leader, for example from kX; Variable Heavy Chain=Variable region of the heavy chain of the antibody of interest, flanked by restriction sites; hIG1 Constant Heavy=cDNA of the human IgG1 constant region; SV40 pA=SV40 polyadenylation sequence; BGH pA=BGH polyadenylation sequence; Light Chain=Variable and constant regions of either lambda or kappa antibody of interest, flanked by restriction sites; and rEF1 alpha=rat EF1 alpha promoter (introns and exons are annotated for the EF1 alpha promoters and the leaders).

FIG. 15 shows a diagram of an exemplary antibody expression vector referred to herein as pEXCEL/ITR for transient expression or integration of antibody expression cassettes into polyclonal cell populations containing the following elements: Left ITR and Right ITR=Inverted Terminal Repeat sequences from AAV2; ColE1 ori=bacterial origin of replication; CMV=CMV enhancer; hFerL=hFerL eukaryotic core promoter, driving expression of the resistance gene; EM7=bacterial promoter driving expression of the resistance gene; Neo/Kan: Neomycin (eukaryotic)/Kanamycin (prokaryotic) resistance gene; B globin pA=Beta globin polyadenylation sequence; hEF1 alpha=human EF1 alpha promoter; Heavy Leader=leader, for example from VhX; Light Leader=leader, for example from kX; Variable Heavy Chain=Variable region of the heavy chain of the antibody of interest, flanked by restriction sites; hIG1 Constant Heavy=cDNA of the human IgG1 constant region; BGH pA=BGH polyadenylation sequence SV40 pA=SV40 polyadenylation sequence; Light Chain=Variable and constant regions of either lambda or kappa antibody of interest, flanked by restriction sites; and rEF1 alpha=rat EF1 alpha promoter (introns and exons are annotated for the EF1 alpha promoters and the leaders).

Figure 16:
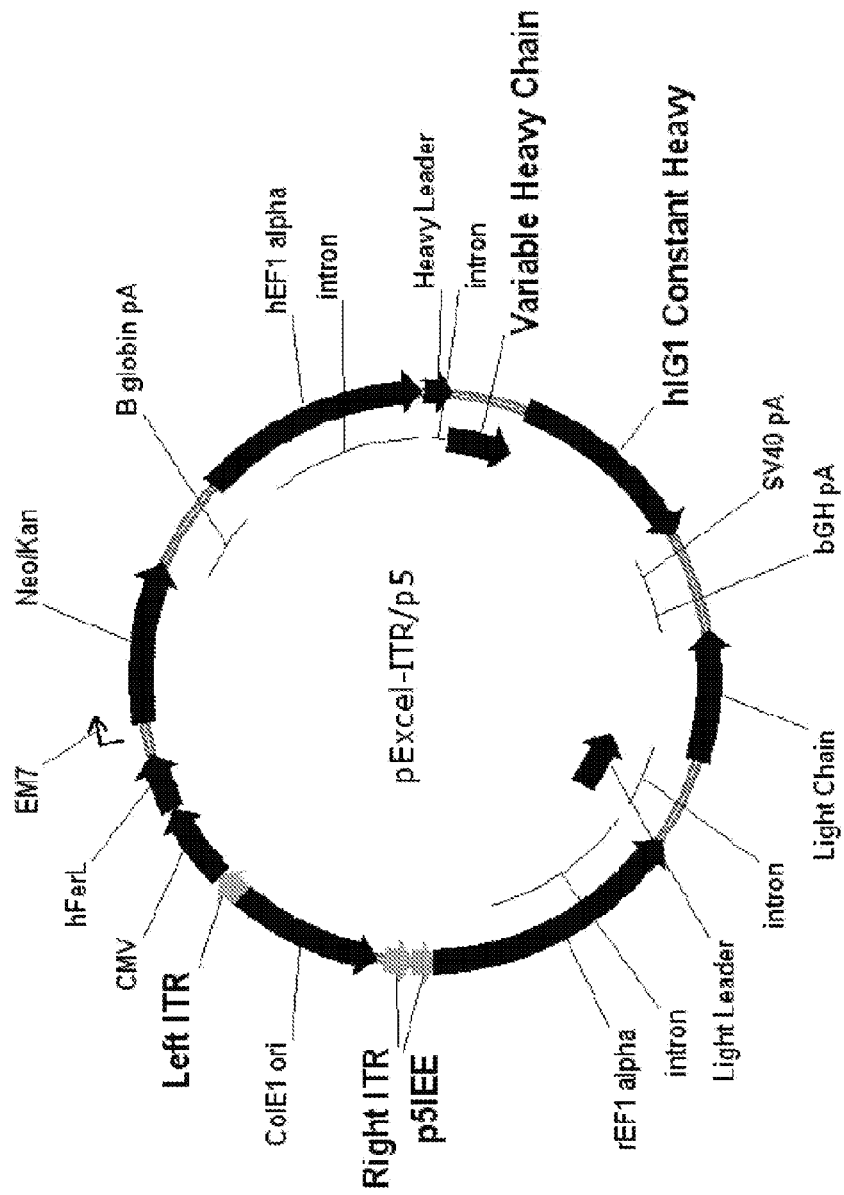
FIG. 16 is a schematic representation of a pEXCEL-ITR/p5 comprising each of the elements of pEXCEL-ITR plus a pSIEE: p5 Integration Efficiency Element from the p5 promoter region of AAV2.

FIG. 16 is a diagram of an exemplary antibody expression vector referred to herein as pEXCEL-ITR/p5 for transient expression or integration of antibody expression cassettes into polyclonal cell populations containing each of the elements of pEXCEL-ITR plus a p5IEE: p5 Integration Efficiency Element from the p5 promoter region of AAV2. This element may be place next to an ITR sequence. Alternatively, the p5 element may replace one or both of the ITR sequences.

FIG. 17 is a diagram of an exemplary Rep78 vector, referred to herein as pExcel-Rep78 vector. The pExcel-Rep 78 vector contains the following elements: SV40 promoter=eukaryotic promoter from Rep78; Rep78=coding sequence of Rep78 from AAV2; SV40 late pA=late polyadenylation sequence from SV40; Amp=Ampicillin resistance gene and bacterial promoter; and ORI=initiation site for a bacterial origin of replication.

Following the construction of the recombinant retroviral vector, the retrovector is introduced into a packaging cell line. Packaging cell lines provide proteins required in trans for the packaging of the viral genomic RNA into viral particles having the desired host range (i.e., the viral-encoded gag, pol and env proteins). The host range is controlled, in part, by the type of envelope gene product expressed on the surface of the viral particle. Packaging cell lines may express ecotrophic, amphotropic or xenotropic envelope gene products. Alternatively, the packaging cell line may lack sequences encoding a viral envelope (env) protein. In this case the packaging cell line can package the viral genome into particles which lack a membrane-associated protein (e.g., an env protein). In order to produce viral particles containing a membrane associated protein, which can permit entry of the virus into a cell, the packaging cell line containing the retroviral sequences is transfected with sequences encoding a membrane-associated protein (e.g., the G protein of vesicular stomatitis virus (VSV)). The transfected packaging cell can then produce viral particles which contain the membrane-associated protein expressed by the transfected packaging cell line; these viral particles, which contain viral genomic RNA derived from one virus encapsidated by the envelope proteins of another virus, are said to be pseudotyped virus particles.

When single-stranded DNA viral vectors are used, e.g., an AAV vector, the vector is cotransfected with an unrelated helper virus such as an adenovirus, a herpesvirus or vaccine to promote productive infection of host cells. In an exemplary embodiment, recombinant AAV virons can be produced in a host cell which has been transfected with both an AAV vector and an AAV helper plasmid. The AAV helper plasmid generally includes the AAV rep and cap proteins, but lacks AAV ITRs. Thus, the AAV helper plasmid cannot replicate or package itself. The AAV vector includes the gene of interest flanked by AAV ITR sequences which provide for viral replication and packaging functions. After the helper plasmid and the AAV vector comprising the nucleic acid of interest are co-transfected into the a host cell using methods well-known in the art, the host cell is infected with a helper virus to transactivate the AAV promoters present on the helper plasmid which direct the expression of the AAV rep and cap proteins. Recombinant AAV virons comprising the nucleic acid of interest can then be purified and used to infect host cells at a desired multiplicity of infection to produce high copy number per cell. As described below, host cells may be repetitively transduced with the same AAV vector and/or a library of AAV vectors.

II. Host Cells

It is contemplated that a variety of host cells suitable for transduction with viral vectors (e.g., retrovectors, AAV vectors, etc.) may be used. Exemplary host cell lines include mammalian cell lines such as Chinese hamster ovary (CHO) cells, monkey kidney CV1 (COS) cells, baby hamster kidney (BHK) cells, bovine mammary epithelial cells, human embryonic kidney (HEK) cells, human cervical carcinoma (HeLa) cells, mouse sertoli cells (TM4), African gene monkey kidney cells (VERO-76), canine kidney cells (MDCK), buffalo rat liver cells (BRL3A), human liver cells (Hep G2), human lung fibroblast cells (WI-38, IMR-90 or MRC-5), mouse mammary tumor cells (MMT 060562), TR1 cells, rat fibroblast cells, and myeloma cells.

In addition to mammalian cells, insect cell lines, amphibian cell lines, and plant cells may also be used. Examples of suitable inset cell lines include, but are not limited to Sf cells (e.g., Sf9 and Sf21 cell lines, and the High Five™ cell line) and mosquito cell lines (e.g., MOS-55 cell line).

III. Transformation Methods and Generation of Cell Populations

In an exemplary embodiment, viral vectors encoding at least one protein of interest or a library of proteins of interest may be used to transform a host cell genome (e.g., a host cell genomic DNA). For example, a host cell may be transduced with a retroviral vector and a retroviral integrase protein, or alternatively, with a single-stranded DNA viral vector (e.g., an AAV vector) and a rep protein, at a multiplicity of infection of at least one, at least 2, at least 5, at least 10 or more viral vectors per cell. Multiplicities of infection of about 10 to about 1,000,000 may be used to produce genomes of an infected host cell containing between about 2 to about 100 copies of the integrated vectors. In some embodiments, a multiplicity of infection of about 10 to about 10,000 is used.

In an exemplary embodiment, one or more host cells may be repetitively transformed, e.g., the host cells are transduced at least 2, 3, 4, 5, 6, 7, 8, 9, 10, 15, 20 or more times with the same viral vector (e.g., a retrovector, AAV vector, etc.) such as described in U.S. Pat. Nos. 6,852,510 and 7,378,273. It is contemplated that the use of multiple, repetitive transductions on the same cell population increases the percentage of host cells containing at least one copy of the integrated vector and may be used to produce host cell populations containing multiple integrated copies. Without wishing to be bound by theory, multiple, repetitive transformations may also increase protein production from the resulting cell population.

Methods for transforming host cells are well-known in the art. Briefly, host cells are exposed to medium containing the infectious vectors for a sufficient period of time to allow for infection and subsequent integration of the one or more genes of interest into the host cell genome. Persons skilled in the art understand that the amount of integration may be maximized by manipulating (1) the volume of medium used to overlay the host cells (e.g., a small volume is used), (2) the amount of time that the host cells are exposed to the vector, (3) the confluency of the host cells, and (4) the multiplicity of infection.

As described herein, in some embodiments, a library of vectors is used to transform a population of host cells. When a host cell is transformed with more than one vector, transformation of the more than one vector may be at the same time (e.g., the host cells are exposed to a solution containing the more than one vector, e.g., the library of vectors) or at different times (e.g., sequentially). When host cells are transformed sequentially with each vector (e.g., a viral vector), the host cell is transfected with a first vector, a period of time is allowed to pass, and the host cells are then transfected with any subsequent vector. In some embodiments, a host cell may be repetitively transformed with a first vector before the host cell is transformed (e.g., repetitively transformed) with any additional vectors.

In an exemplary embodiment, the transformation methods disclosed herein do not require the use clonal selection of an individual progenitor cell (e.g., an individual cell clone) and/or the production of a cell line to identify and select cells containing the integrated gene of interest. As described above, the vectors of the invention may not include a selection marker. The method disclosed herein utilizes multiple, repetitive transformations to generate host cell populations that contain at least 80%, 85%, 90%, 95%, 98%, 99%, and 100% of cells containing at least one integrated copy of the one or more genes of interest.

In some embodiments, a cell population may comprise both transformed host cells and non-transformed host cells. When non-transformed host cells are present, the disclosed methods may further comprise a selection step to select the subset of transformed cells in the population. The selection step may be a negative or positive selection. Exemplary negative selection markers include, but are not limited to, G418, blasticidin, puromycin, hygromycin and zeocin. Exemplary positive selection include the use of enzymes capable of making an essential amino acid that can be withheld from the culture media. The selection step may occur prior to mixing a plurality of individual cell populations. Alternatively, the selection step may occur after the mixing of a plurality of individual cell populations. Selection may also be performed on cell populations generated using a plurality of vectors in a single round of transformation (e.g., where each vector in the single round of transformation encodes more than one protein of interest).

Host cells integrated with at least one or more copies of the gene of interest can be expanded using standard techniques well-known in the art, if further cell numbers are desired. Individual cell populations may be expanded to about 1 million cells, about 5 million cells, about 10 million cells, about 20 million cells or more cells. In an exemplary embodiment, individual cell populations are expanded to about 10 million cells prior to mixing cell populations as discussed below.

IV. Mixing of Cell Populations to Produce Recombinant Polyclonal Cell Populations At least two individual cell populations, each of which produces a different protein, as generated from the method steps described herein, can be mixed to produce a polyclonal mixture of cells (referred to herein as a "polyclonal cell population"). In an exemplary embodiment, at least two individual cell populations are generated and mixed together to produce a polyclonal cell population capable of producing multiple proteins. A polyclonal cell population may comprise at least 2, 3, 4, 5, 6, 7, 8, 9, 10, 15, 20, 25, 50, 75, 100 or more cell populations each capable of producing a different protein.

The at least two individual cell populations can be mixed in equal numbers (e.g., a 1:1 ratio) or at a ratio different than 1:1 (e.g., a 1:2 ratio, 1:3 ratio, 1:4 ratio, 1:5 ratio, 1:10 ratio or more). It is also contemplated that when three or more individual cell populations are mixed together that the cells may be mixed at, e.g., a 1:1:1 ratio, or any possible variation differing from, e.g., a 1:1:1 ratio.

Polyclonal cell populations may be further expanded using methods well-known in the art or frozen to form a cell bank (discussed below). The total size of a polyclonal cell population may include at least 100 cells, at least 1,000 cells, at least 10 thousand cells, at least 100 thousand cells, at least 1 million cells, at least 5 million cells, at least 10 million cells, at least 20 million cells, at least 50 million cells or more. In an exemplary embodiment, a recombinant polyclonal cell population can be generated from individual cell populations (each capable of producing a different protein) where each individual cell population is about 1 million cells. For example, if the recombinant polyclonal protein composition includes 5 different proteins, the size of the recombinant cell population would be least 5 million cells (e.g., approximately one million cells from each of the five individual cell lines). It is contemplated that the size of the polyclonal cell population is large enough that a Gaussian growth curve of one transfected cell population producing one protein is identical or substantially identical to the transfected cell population producing a second (or third, etc.) protein. Stability of the polyclonal cell populations described herein is achieved by using large populations of transfected cells and mixing large numbers of individual cell populations (e.g., about 1 million or more cells per individual cell population) to produce a recombinant polyclonal cell population.

V. Banking Recombinant Cell Populations

Recombinant cell populations (e.g., cell populations expressing a single recombinant polypeptide and polyclonal cell populations containing at least two different cell populations capable of producing different proteins may be banked (i.e., frozen and stored) for future testing, screening, manufacturing, and/or use. Cell populations may be aliquoted and frozen in individual vials or ampoules (e.g., to produce frozen stocks) using methods well-known in the art. The size of the aliquot, the number of cells per vial, and the number of vials (or ampoules) may vary depending on the desired use of the cell population. In some embodiments, a cell population may be banked at total cell counts of about 1 million, about 5 million, about 10 million, or about 20 million cells per vial. In an exemplary embodiment, polyclonal cell populations are banked at a total cell count of about 10 million cells per vial.

It is contemplated that a cell population (e.g., a polyclonal cell population) may be banked subject to further testing and validation of the protein composition (e.g., a polyclonal protein composition). Upon validation of a polyclonal protein composition produced by the methods described herein it is contemplated that one or more frozen ampoules of the cell population (e.g., the monoclonal or the polyclonal cell population) may be thawed and expanded using standard cell culture techniques. Such steps may be taken to establish a manufacturing cell line capable of producing large scale volumes of a given polyclonal protein composition (e.g., a manufacturing cell line for producing a polyclonal protein composition for therapeutic use).

In an certain embodiments, individual cell populations expressing a single protein (e.g., a single antibody) are not banked (i.e., frozen and stored).

VI. Recombinant Polyclonal Protein Compositions

A recombinant polyclonal protein composition produced by the methods described herein contain a mixture of proteins.

In some embodiments, the polyclonal protein composition is a mixture of antibodies that bind to different antigenic epitopes on one or more target proteins. For example, a polyclonal cell population may comprise at least 2, 3, 4, 5, 6, 7, 8, 9, 10, 15, 20, 25, 50, 75, 100 or more cell populations capable of producing a polyclonal antibody composition that binds to at least 2, 3, 4, 5, 6, 7, 8, 9, 10, 15, 20, 25, 50, 75, or 100 different antigenic epitopes. When binding to different antigenic epitopes, the epitopes can be on the same or different target proteins (e.g., at least 2, 3, 4, 5, or more different target proteins).

Exemplary polyclonal antibody compositions that target more than one polypeptide include, without limitation, compositions that target polypeptides in the same molecular pathway (e.g., a ligand, its cognate receptor, and/or a downstream effector molecule), polypeptides that have redundant functions (e.g., two ligands that act through the same receptor), or polypeptides where each is expressed on the surface of the same cell (e.g., the at least two polypeptides are both expressed on same disease-associated cell, e.g., a tumor cell). In some embodiments, the two or more target polypeptides may be otherwise unrelated polypeptides except for association with the same disease, disorder, or condition.

In some embodiments, the recombinant polyclonal protein composition is a recombinant polyclonal antibody composition containing a mixture of antibodies that target a single polypeptide (e.g., the mixture of antibodies may target the same, similar (e.g., partially overlapping epitope), or different antigenic epitopes on the same target polypeptide). In some embodiments, the recombinant polyclonal antibody composition may target both wild type and mutant forms of a polypeptide (e.g., known mutants associated with resistance to therapy, e.g., cancer treatments, or increased disease severity).

Exemplary antibody polypeptides of the invention comprise an immunoglobulin heavy chain and an immunoglobulin light chain to form a tetrameric antibody comprising six complementarity determining regions (CDRs) (i.e., three CDRs on the immunoglobulin heavy chain and three CDRs on the immunoglobulin light chain). It is contemplated that the immunoglobulin heavy chain and light chain sequences of the invention may correspond to natural antibody sequences or genetically engineered antibody sequences including chimeric antibodies, humanized antibodies, fully human antibodies, and multispecific antibodies (e.g., bispecific antibodies). It is also contemplated that the polypeptide of interest may correspond to antigen-binding fragments such as Fab, Fab', F(ab')$_2$, or Fv fragments. Methods for reducing or eliminating the antigenicity of antibody and antibody fragments are well-known in the art. In some embodiments, a polyclonal antibody composition may include a combination of tetrameric, intact antibodies (e.g., naturally occurring and/or genetically engineered antibodies) and/or antigen-binding fragments thereof.

In some embodiments, one or more of the antibodies in the polyclonal antibody composition may be chemically conjugated to other moieties such as detectable labels or effector molecules such as small molecules (e.g., toxins).

Polyclonal antibody compositions may contain immunoglobulin heavy chains of more than one isotype. For example, the immunoglobulin heavy chains may include any one of the following isotypes: IgG1, IgG2, IgG3, IgG4, IgA1, IgA2, IgM, IgD and IgE. Upon mixing of individual cell populations, the recombinant polyclonal mixture may comprise the immunoglobulin heavy chain sequences of the same or different isotypes. In some embodiments, the recombinant polyclonal antibody composition may contain at least two or more different isotypes.

Polyclonal antibody compositions can be purified using methods well-known in the art. Exemplary methods include gel filtration, affinity chromatography, ion exchange chromatography, and hydrophobic interaction chromatography. The selected purification method may depend on whether all of the antibodies in the polyclonal antibody composition are of the same or related isotypes (e.g., IgG1, IgG2, and IgG4). When the antibodies are of the same or related isotype (e.g., all of the antibodies are IgG antibodies), the antibodies may be purified using Protein A affinity chromatography. If the antibodies are of different (and unrelated) isotypes, gel filtration may be used to purify the polyclonal antibody composition.

In some embodiments, the polyclonal protein composition is a mixture of proteins for use as a vaccine. The polyclonal composition may include recombinant proteins that resemble one or more infectious agents of the same pathogen, variants of a given infectious agent (e.g., mutant forms, isoforms, etc.), or different infectious agents. The protein components of a polyclonal protein composition may include a combination of protein targets or agents that are known or suspected to cause disease. Polyclonal protein compositions can be purified using methods well-known in the art, including, but not limited to gel filtration, affinity chromatography, ion exchange chromatography, and hydrophobic interaction chromatography.

The stability of a polyclonal protein composition including, but not limited to a polyclonal antibody composition, a polyclonal vaccine composition, may be determined using methods well-known in the art. Exemplary methods include ion exchange chromatography, high-performance liquid chromatography (HPLC), papain digestion followed by 2-D gel analysis, microarray, quantitative PCR (qPCR), and an ELISA assay. It is contemplated that banked polyclonal protein compositions may be monitored periodically over time to assay the stability of the individual proteins that constitute the recombinant polyclonal protein composition.

In certain embodiments, stability of polyclonal protein mixtures can be analyzed by high-performance liquid chromatography (HPLC). Samples may be prepared as described below: cells (e.g., FreeStyle 293-F culture (Invitrogen)) may be subjected to centrifugation at 400×g for 5 minutes, the supernatant may then be subjected to flash freezing and storage at −20° C., and subsequent filtration, e.g., with a 96 well filter plates (3M Empore, Catalog #6065). HPLC (Ultimate 3000 RSLC, Dionex) analysis may be conducted using a WCX-10 ProPac column (Dionex, Catalog #016830), a flow rate of 1 ml/min, column temperature of 30° C., and detection of 220/280 nm. Antibody proteins may be eluted from the ion exchange column with a linear gradient between 20 mM 2-(N-morpholino)ethanesulfonic acid (MES), pH 5.6 (buffer A) and 20 mM MES/1M NaCl, pH 5.6 (buffer B). The chromatography analysis of each supernatant sample may be executed in sequential steps such as (total of 14 minutes) a gradient from 5% to 33% Buffer B over 7 minutes, a gradient from 33% to 100% Buffer B over 0.5 minute, 100% Buffer B for 1 minute, a gradient from 100% to 5% Buffer B over 0.5 minute, and 5% of Buffer B for 5 minutes. The Chromeleon Console program (Dionex) may be used to compute the values of the peaks as a function of mAU (A280) and retention time (minutes). Using these chromatography conditions, the antibody proteins may be eluted at distinct retention times. In another exemplary purification protocol, the antibody protein may be expressed in FreeStyle 293-F cells (Invitrogen) using 293fectin Transfection Reagent (Invitrogen, Catalog #12347-019) as per manufacturer's instructions and purified using the HiTrap MabSelect (GE Healthcare, catalog #28-4082-53) column and the buffer may be exchanged with the Bioscale Mini Bio Gel P6 Desalting Cartridge (Biorad, Catalog #732-5304). The eluted antibody proteins may be quantified by A280, mixed, and analyzed by HPLC.

VII. Use of Recombinant Polyclonal Protein Compositions

Recombinant polyclonal protein compositions of the invention can be used to treat various diseases and disorders including cancer (e.g., breast, lung, non-small cell lung, ovarian, prostate, cervical, colorectal, pancreatic, liver, gastric, and head and neck cancers). For example, cancer cells may be exposed to a therapeutically effective amount of a polyclonal protein composition (e.g., a polyclonal antibody composition) to inhibit or reduce proliferation of the cancer cell. In some embodiments, a recombinant polyclonal antibody composition of the invention inhibits cancer cell proliferation by at least 40%, 50%, 60%, 70%, 80%, 90%, 95%, 98%, 99% or 100%.

In other embodiments, a polyclonal protein composition of the invention may be used to treat bacterial and/or viral infections and infectious proteins, such as prions and toxins.

As used herein, "treat, "treating" and "treatment" mean the treatment of a disease in a mammal, e.g., in a human. This includes: (a) inhibiting the disease, i.e., arresting its development; and (b) relieving the disease, i.e., causing regression of the disease state; and (c) curing the disease.

Generally, a therapeutically effective amount of active component is in the range of 0.01 mg/kg to 100 mg/kg, e.g., 1 mg/kg to 100 mg/kg, 1 mg/kg to 10 mg/kg. The amount administered will depend on variables such as the type and extent of disease or indication to be treated, the overall health of the patient, the in vivo potency of the antibody, the pharmaceutical formulation, and the route of administration. The initial dosage can be increased beyond the upper level in order to rapidly achieve the desired blood-level or tissue level. Alternatively, the initial dosage can be smaller than the optimum, and the daily dosage may be progressively increased during the course of treatment. Human dosage can be optimized, e.g., in a conventional Phase I dose escalation study designed to run from 0.5 mg/kg to 20 mg/kg. Dosing frequency can vary, depending on factors such as route of administration, dosage amount and the disease being treated. Exemplary dosing frequencies are once per day, once per week and once every two weeks. A preferred route of administration is parenteral, e.g., intravenous infusion. Formulation of polyclonal protein-based drugs (e.g., a polyclonal antibody, a vaccine, etc.) is within ordinary skill in the art. In some embodiments, a polyclonal protein composition (e.g., polyclonal antibody composition) is lyophilized and reconstituted in buffered saline at the time of administration.

For therapeutic use, a polyclonal protein composition of the invention preferably is combined with a pharmaceutically acceptable carrier. As used herein, "pharmaceutically acceptable carrier" means buffers, carriers, and excipients suitable for use in contact with the tissues of human beings and animals without excessive toxicity, irritation, allergic response, or other problem or complication, commensurate with a reasonable benefit/risk ratio. The carrier(s) should be "acceptable" in the sense of being compatible with the other ingredients of the formulations and not deleterious to the recipient. Pharmaceutically acceptable carriers include buffers, solvents, dispersion media, coatings, isotonic and absorption delaying agents, and the like, that are compatible with pharmaceutical administration. The use of such media and agents for pharmaceutically active substances is known in the art.

Pharmaceutical compositions containing polyclonal proteins (e.g., antibodies, vaccines) of the invention can be presented in a dosage unit form and can be prepared by any suitable method. A pharmaceutical composition should be formulated to be compatible with its intended route of administration. Examples of routes of administration are intravenous (IV), intradermal, inhalation, transdermal, topical, transmucosal, and rectal administration. A preferred route of administration for polyclonal antibodies is IV infusion. Useful formulations can be prepared by methods well known in the pharmaceutical art. For example, see *Remington's Pharmaceutical Sciences,* 18th ed. (Mack Publishing Company, 1990). Formulation components suitable for parenteral administration include a sterile diluent such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as EDTA; buffers such as acetates, citrates or phosphates; and agents for the adjustment of tonicity such as sodium chloride or dextrose.

For intravenous administration, suitable carriers include physiological saline, bacteriostatic water, Cremophor ELTM (BASF, Parsippany, N.J.), or phosphate buffered saline (PBS). The carrier should be stable under the conditions of manufacture and storage, and should be preserved against microorganisms. The carrier can be a solvent or dispersion medium containing, for example, water, ethanol, polyol (for example, glycerol, propylene glycol, and liquid polyethylene glycol), and suitable mixtures thereof.

Pharmaceutical formulations preferably are sterile. Sterilization can be accomplished, for example, by filtration through sterile filtration membranes. Where the composition is lyophilized, filter sterilization can be conducted prior to or following lyophilization and reconstitution.

EXAMPLES

The following Examples are merely illustrative and is not intended to limit the scope or content of the invention in any way.

Example 1

Production of Stable Polyclonal Cell Populations Using AAV Rep Protein to Promote Stable Expression of Exogenous DNA Sequences A. AAV Rep protein enhances stable expression of exogenous DNA sequences in cultured cells.

The purpose of this example was to determine if the AAV Rep protein enhances stable expression of exogenous DNA sequences in cultured cells.

GFP was expressed in Freestyle 293 cells following co-transfection of pExcel-ITR:GFP with varying concentrations of pAAV2-Rep78. Freestyle 293 cells ($2 \times 10^6$) were co-transfected with 2 μg pExcel-ITR:GFP and 2 μg, 40 ng, 20 ng, 10 ng or 4 ng of pAAV2-Rep78 using 293-Fectin following the manufacturer's directions. Cells were cultured for 25 days in the absence of any selection. Every 3 to 4 days GFP expression was assessed by FACS analysis. The percentage of cells expressing GFP on day 17, 21 and 25 were averaged and the error bars represent the standard deviation as shown in FIG. 1. Vector alone (1:0 of the pExcel-ITR:GFP to pRep78) resulted in approximately 1% integration as shown in FIG. 1. Although high levels of Rep78 were toxic to the cells, Rep78 when administered in less toxic doses mediated a higher overall stable integration efficiency, (for example, the 1:1 concentration ratio of pExcel-ITR:GFP to pRep78 as shown in FIG. 1 only resulted in a slight increase in AAV rep 78 mediated integration compared to integration with vector alone (1:0 in FIG. 1)), titration of pRep78 revealed concentrations of pRep78, e.g., 1:50 and 1:100, that enhanced stable expression by approximately 5-fold.

B. Non-viral AAV integration results in stable antibody expression.

Figure 2:
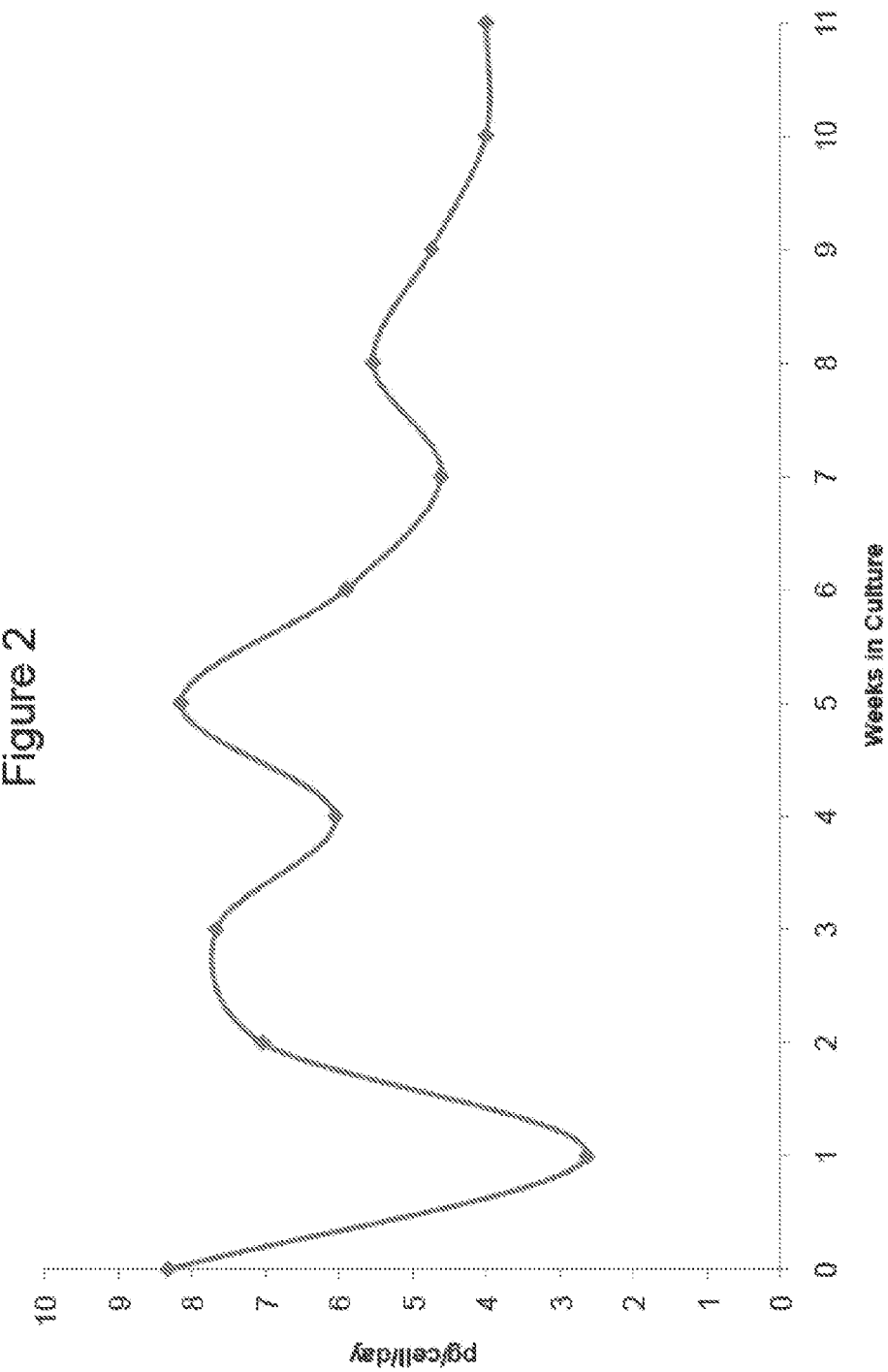
FIG. 2 is a graph showing that non-viral AAV integration results in stable antibody expression over an 11 week period.

The purpose of this example was to investigate whether non-viral AAV integration results in stable antibody expression. Freestyle 293 cells ($30 \times 10^6$) were co-transfected with 30 μg pExcel-ITR:5.55.D2 (which expresses anti-*S. aureus* delta toxin IgG1) and 150 ng pAAV2-Rep78 using 293-Fectin following the manufacturer's directions and IgG1 production was monitored over time. Three days post transfection, cells were passaged into growth media containing 500 μg/mL G418. Fc-specific ELISA of cell culture supernatant was performed twice a week. The total pg/ml of IgG1 at each time point was divided by the average cell number/day in culture. As shown in FIG. 2, the relative expression as measured as picogram antibody produced per cell per day (pg/cell/day) remains between 4 and 8 pg/cell/day over an eleven week period. The cell density and viability appeared to drop during the G418 selection period impacting antibody production of the cells during this time period but by day 21 (week 3) cell density and viability recovered to pre-transfection levels, while the expression levels approximate the transient transfection levels (time=0) at 14 days post G418 selection initiation.

Additional experiments were also performed with a total of five different antibody producing cell populations (conducted in duplicate) monitoring stability over an 11 week period. The expression levels of these populations remained between 3 and 10 pg/cell/day over the course of the experiment.

Figure 10:
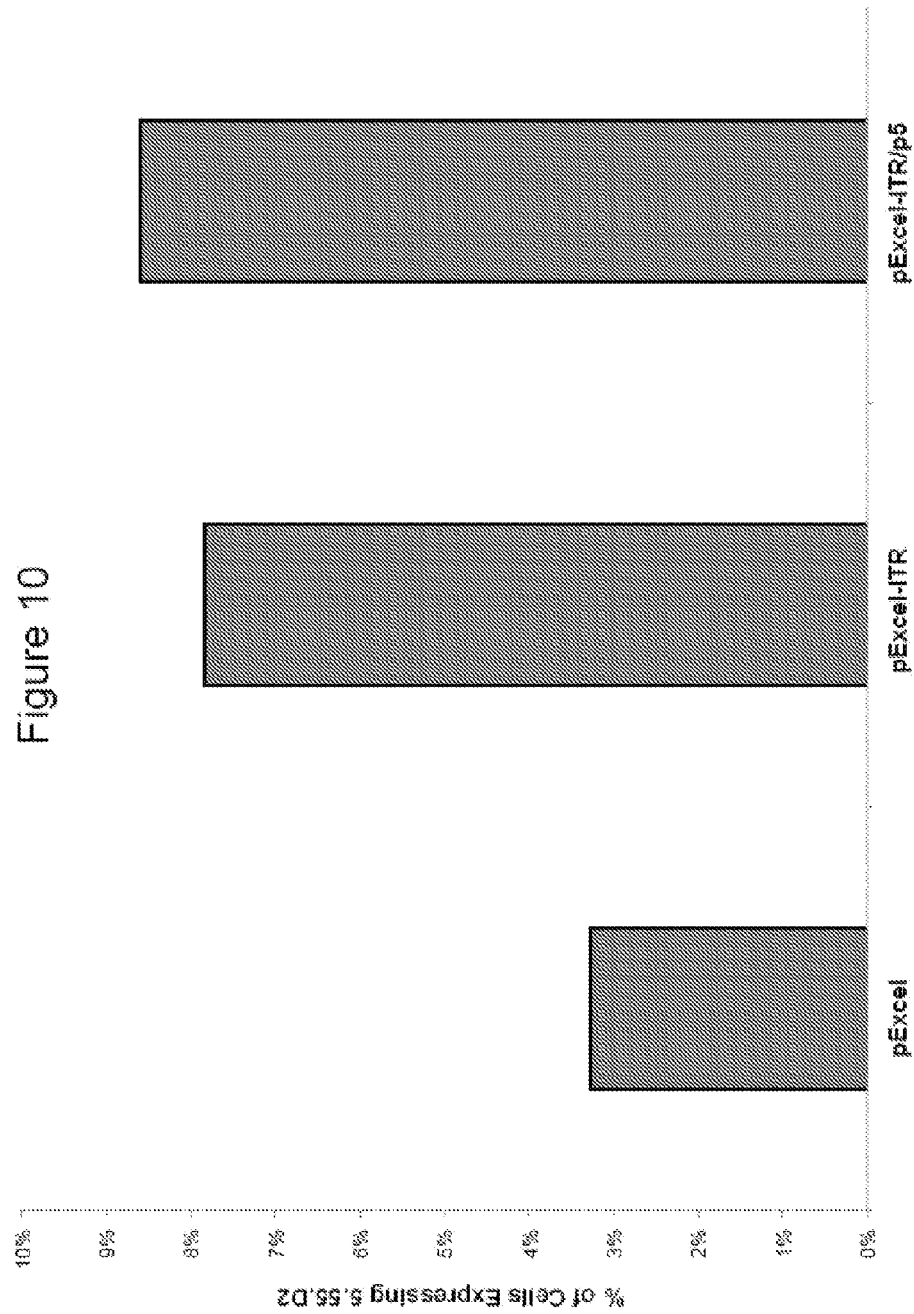
FIG. 10 is a graph demonstrating that AAV elements enhance integration efficiency of exogenous DNA into cell genomes.

The resulting cell populations were not a clonal cell line, but rather represent a bulk cell population made up of cells having a diverse distribution of integration events mediated mostly by the Rep78 protein (as indicated by results shown in FIG. 1 and FIG. 10). These results suggest that at a cell concentration of 4×10$^6$ cells/ml, it would take 31 days in this experiment to fill a 10,000 L volume. By eleven weeks, this is equivalent to 7.75×10$^{12}$ Liters, or the equivalent of 7.75× 10$^7$ ten thousand liter production vessels. In subsequent examples of polyclonal population mixtures, time periods are shown to exemplify being stable through the production of a cell population numbering sufficient to populate a 10,000 L production vessel. The data also suggest that as shown in FIG. 2, these cell populations can produce antibodies stably for many multiples of that production volume.

C. Production of Stable Polyclonal Cell Mixtures

Individual antibody components of recombinant polyclonal cell populations were monitored over time to assess the stability various polyclonal cell populations produced using AAV Rep Protein integration.

Figure 3:
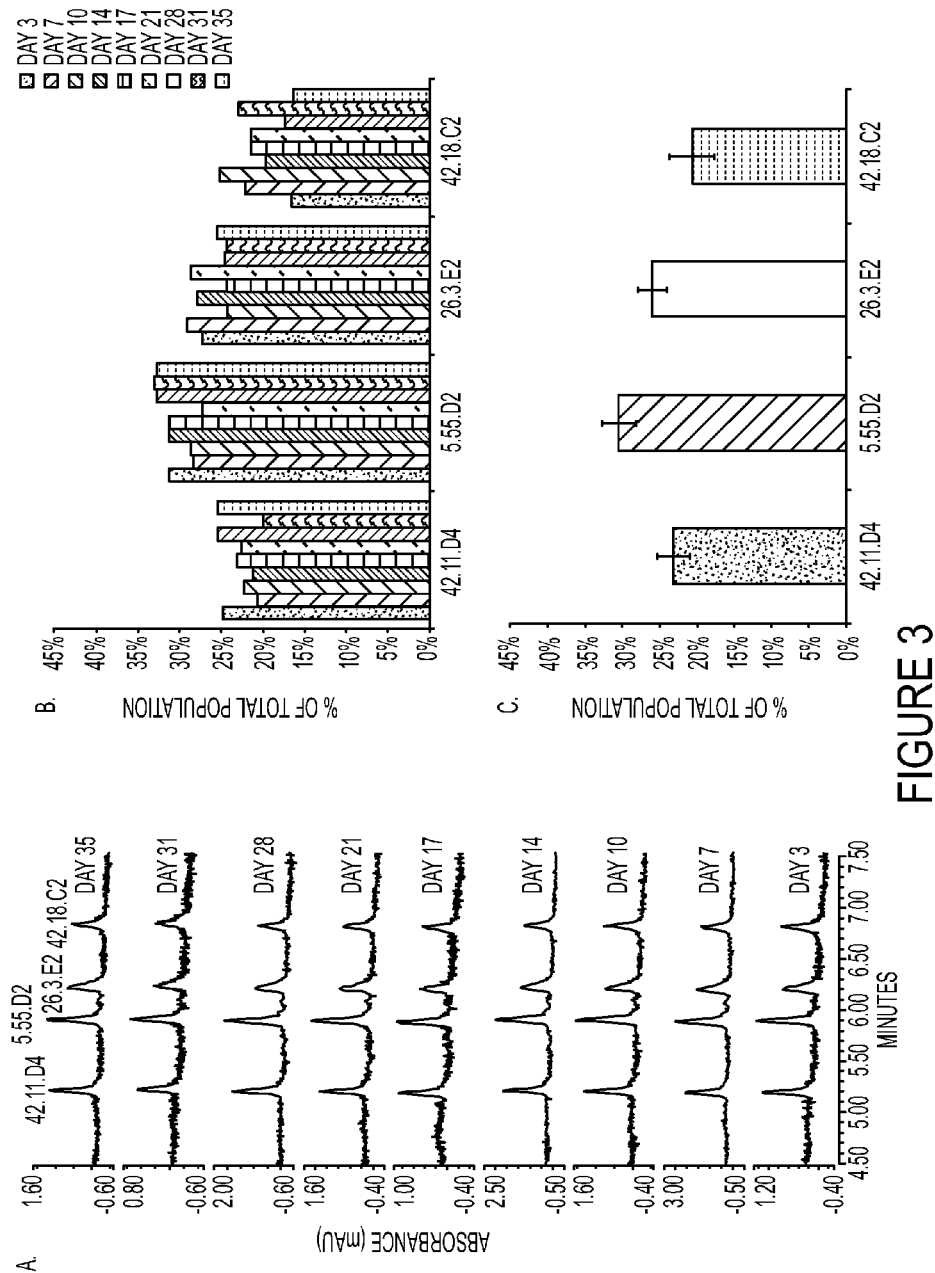
FIG. 3 is a series of chromatographs (A) and graphs (B-C) showing the production of stable polyclonal cell population containing produced using the pExcel-ITR vector system. The stable polyclonal cell populations contains a mixture of four different cell populations each expressing a different antibody, e.g., antibodies 42.11.D4, 5.55.D2, 26.3.E2 and 42.18.C2. (A) shows a series of IEX-HPLC chromatographs obtained between Day 3 and Day 35 following generation of the polyclonal cell population. (B) shows the area under the peak of each antibody which was used to calculate the percentage of each antibody within the total population over time. (C) shows the average percentage of each antibody within the population over the entire course of the experiment.

Freestyle 293 cell populations expressing four different antibodies with the following antibody designations were generated using the pExcel-ITR vector system as described in FIG. 2: 42.11.D4 (a *Bordetella pertussis* specific antibody), 5.55.D2 (a *S. aureus* specific antibody), 26.3.E2 (a bovine kappa-casein specific antibody) and 42.18.C2 (a Tetanus toxin specific antibody). Twenty-one days post-transfection, an equal number of cells (2×10$^5$/mL) of each of the four populations was mixed and the time was designated Day 0. As shown in FIG. 3, at the indicated time points (e.g., Day 3, Day 7, Day 10, Day 14, Day 17, Day 21, Day 28, Day 31, Day 35), IEX HPLC analysis of cell culture supernatants was performed. Stacked HPLC chromatograms for each time point are shown in FIG. 3A. The area under the peak of each antibody from the HPLC analysis was used to calculate the percentage of each antibody within the total population over time as shown in FIG. 3B. The percentage of each antibody within the population over the entire course of the experiment was averaged and the standard deviation is shown in FIG. 3C. For example, in FIGS. 3B-C, cells expressing antibody 42.11.D4 are 23.1%±2.1% of the total cell population; cells expressing antibody 5.55.D2 are 30.3%±2.2% of the total cell population; cells expressing antibody 26.3.E2 are 26.0%±2.1% of the total cell population; and cells expressing antibody 42.18.C2 are 20.6%±3.0% of the total cell population.

The data shown in FIG. 3 indicates that the pExcel-ITR vector system using an AAV Rep78 protein produced a stable polyclonal population consisting of the four antibody populations tested. Each of the four cell populations within the polyclonal population (each expressing a different antibody) were stable through Day 35 relative to one another (e.g., there was very little fluctuation in the total expression any of the given antibodies over the time course as measured by the HPLC profile). There was no skewing or bias of any of the four different populations within the polyclonal observed once the polyclonal population was established.

Polyclonal cell populations were also produced using the pExcel-ITR vector system with the AAV Rep78 protein and a p5 element (referred to herein as pExcel-ITR/p5). Individual antibody components of recombinant polyclonal cell populations were monitored over time to assess the stability of the polyclonal population and determine the effect of the p5 element on the stability of the population.

Figure 4:
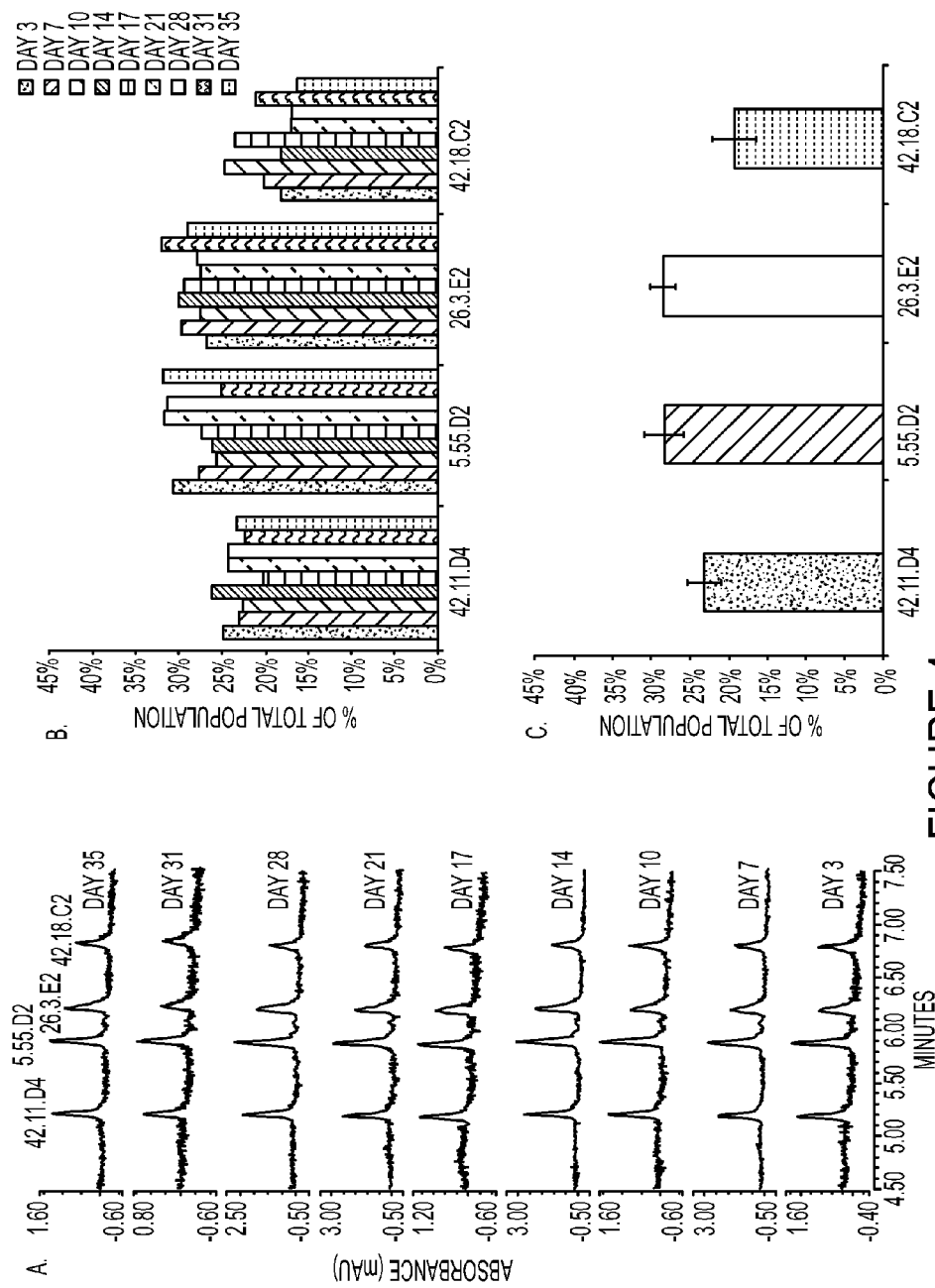
FIG. 4 is a series of chromatographs (A) and graphs (B-C) showing the production of stable polyclonal cell population containing produced using the pExcel-ITR/p5 vector system. The stable polyclonal cell populations contains a mixture of four different cell populations each expressing a different antibody, e.g., antibodies 42.11.D4, 5.55.D2, 26.3.E2 and 42.18.C2. (A) shows a series of IEX-HPLC chromatographs obtained between Day 3 and Day 35 following generation of the polyclonal cell population. (B) shows the area under the peak of each antibody which was used to calculate the percentage of each antibody within the total population over time. (C) shows the average percentage of each antibody within the population over the entire course of the experiment.

Freestyle 293 cell populations expressing four different antibodies with the following antibody designations were generated using the pExcel-ITR/p5 vector system as described in FIG. 3: 42.11.D4, 5.55.D2, 26.3.E2 and 42.18.C2. Twenty-one days post transfection, an equal number of cells (2×10$^5$/mL) of each of the four populations were mixed and the time was designated Day 0. As shown in FIG. 4, at the indicated time points (e.g., Day 3, Day 7, Day 10, Day 14, Day 17, Day 21, Day 28, Day 31, Day 35), IEX HPLC analysis of cell culture supernatants was performed. Stacked HPLC chromatograms for each time point are shown in FIG. 4A. The area under the peak of each antibody from the HPLC analysis was used to calculate the percentage of each antibody within the total population over time as shown in FIG. 4B. The percentage of each antibody within the population over the entire course of the experiment was averaged and the standard deviation is shown in FIG. 4C. For example, in FIGS. 4B-C, cells expressing antibody 42.11.D4 are 23.4%±1.9% of the total cell population; cells expressing antibody 5.55.D2 are 28.6%±2.5% of the total cell population; cells expressing antibody 26.3.E2 are 28.7%±1.6% of the total cell population; and cells expressing antibody 42.18.C2 are 19.4%±2.8% of the total cell population.

The data shown in FIG. 4 indicates that the pExcel-ITR/p5 vector system using an AAV Rep78 protein with a p5 element produced a stable polyclonal population consisting of the four antibody populations tested. The results achieved with the p5 element were similar to those achieved without the p5 element indicating that the p5 element did not change stability for the polyclonal cell population, although the precise mixture of this polyclonal population was slightly different from the one depicted in FIG. 3. In both examples (e.g., using the pEXCEL-ITR system vs. the pEXCEL-ITR/p5 system), cell populations of approximately equal numbers were merely mixed together. Although this can lead to different representations of each antibody in the cell mixture, there was no skewing or bias of any of the four different populations within the polyclonal cell population observed once the polyclonal population was established.

D. Production of Stable Polyclonal Cell Mixtures Prior to Selecting Monoclonal Stable Cell Populations The purpose of this experiment was to investigate whether stable polyclonal cell mixtures could be generated prior to selecting monoclonal stable cell populations. For example, in this experiment, cell populations were mixed to generate a polyclonal cell population without selecting individual stable cell populations using a selectable marker (e.g., the selectable marker neomycin which may be selected in media containing G418).

Figure 5:
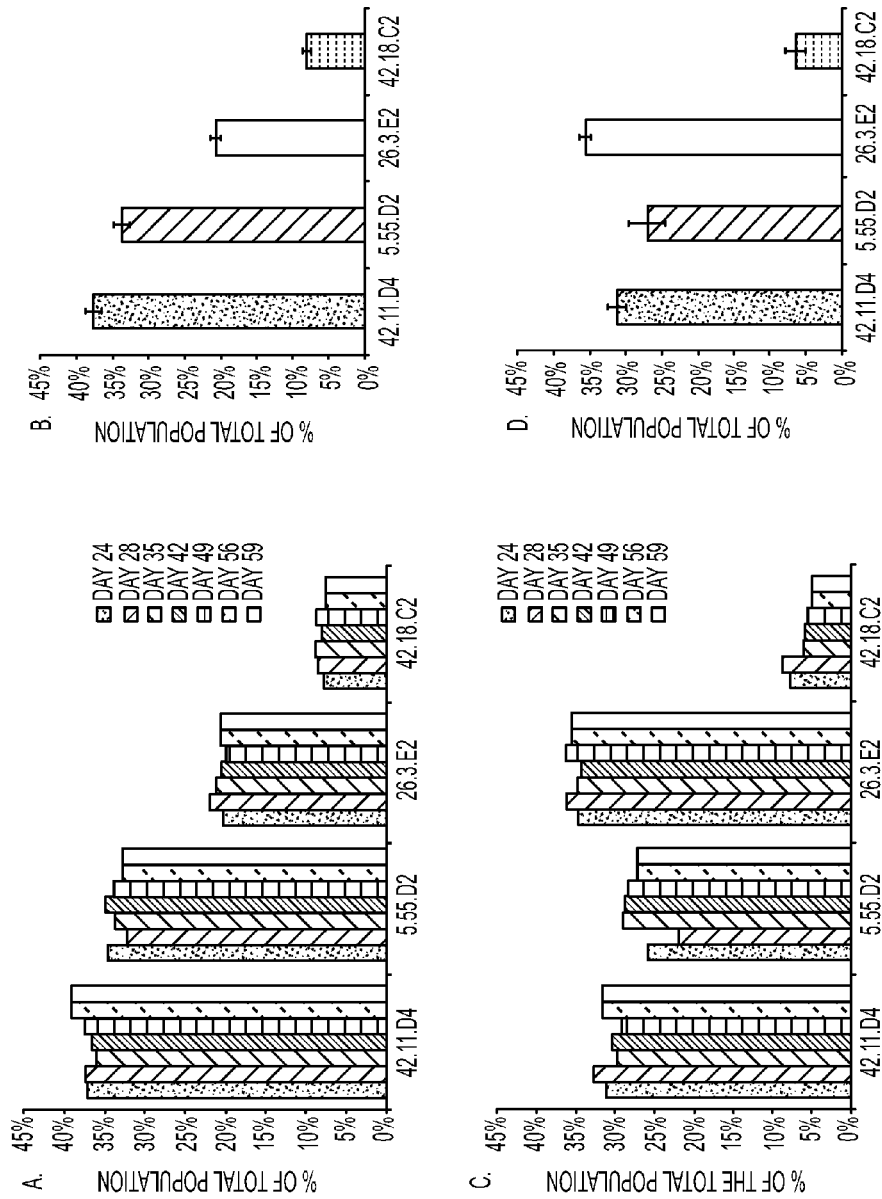
FIG. 5 is a series of graphs demonstrating that stable polyclonal populations can be generated prior to selecting individual monoclonal cell populations. (A) shows the ratio of component antibodies in a polyclonal cell population using the pExcel-ITR vector system where the individual cells were mixed prior to selection using G418. (B) shows the average antibody ratios from (A) over time. (C) shows the ratio of component antibodies in a polyclonal cell population using the pExcel-ITR/p5 vector system where the individual cells were mixed prior to selection using G418. (D) shows the average antibody ratios from (C) over time.

Freestyle 293 cells (30×10$^6$) were transfected with 150 ng pAAV2-Rep78 and 30 µg of either pExcel-ITR (see FIG. 5A-B) or pExcel-ITR/p5 (see FIG. 5C-D) encoding one of the following antibodies: 42.11.D4, 5.55.D2, 26.3.E2 or 42.18.C2. Three days post-transfection, an equal number of cells (2×10$^5$/mL) of each of the four populations were mixed and the time was designated Day 0. Immediately following mixing, cells were passaged into growth media containing 500 µg/mL G418. IEX HPLC analysis of cell culture supernatants was performed at Day 3, Day 7, Day 10, Day 14, Day 17, Day 21, Day 28, Day 31 and Day 35 as described above. The area under the peak of each antibody was used to calculate the percentage of each antibody within the total population over time as shown in FIGS. 5A and 5C. For example, as shown in FIGS. 5A and 5B, antibody 42.11.D4 represents 37.6%±1.1% of the total cell population; antibody 5.55.D2 represents 33.6%±1.0% of the total cell population; antibody 26.3.E2 represents 20.7%±0.7% of the total cell population; and antibody 42.18.C2 represents 8.1%±0.5% of the total cell population. Another example, as shown in FIGS. 5C and 5D, antibody 42.11.D4 represents 31.1%±1.2% of the total cell population; antibody 5.55.D2 represents 27.0%±2.5% of the total cell population; antibody 26.3.E2 represents 35.5%±0.8% of the total cell population; and antibody 42.18.C2 represents 6.4%±1.4% of the total cell population. The percentage of each antibody within the population over the entire course of the experiment was averaged and the standard deviation is shown in FIGS. 5B and 5D.

The data indicate that the polyclonal cell populations are stable when mixed prior to selection with G418. The data also indicate that individual component loss (e.g., any of the single antibody components) is less than 10% for the polyclonal populations (e.g., the loss of cells expressing antibody 42.18.C2 is less than 10% such that expression of antibody 42.18.C2 is not lost in the polyclonal mixture over time). The data also demonstrate that under represented (or otherwise minor cell populations) are not lost over time and remain present in the same rations throughout the time periods tested.

Further experiments were conducted to test for reproducibility in producing stable polyclonal cell populations using the pExcel-ITR vector system. Duplicate polyclonal cell populations were produced. Each individual cell population expressed one of the following antibodies using the pExcel-ITR vector system: 42.11.D4, 5.55.D2, 26.3.E2 and 42.18.C2. Immediately following mixture of the polyclonal cell population containing cells expressing each of the four antibodies as described above, the polyclonal population was split into duplicate cultures and cultured in parallel.

Figure 6:
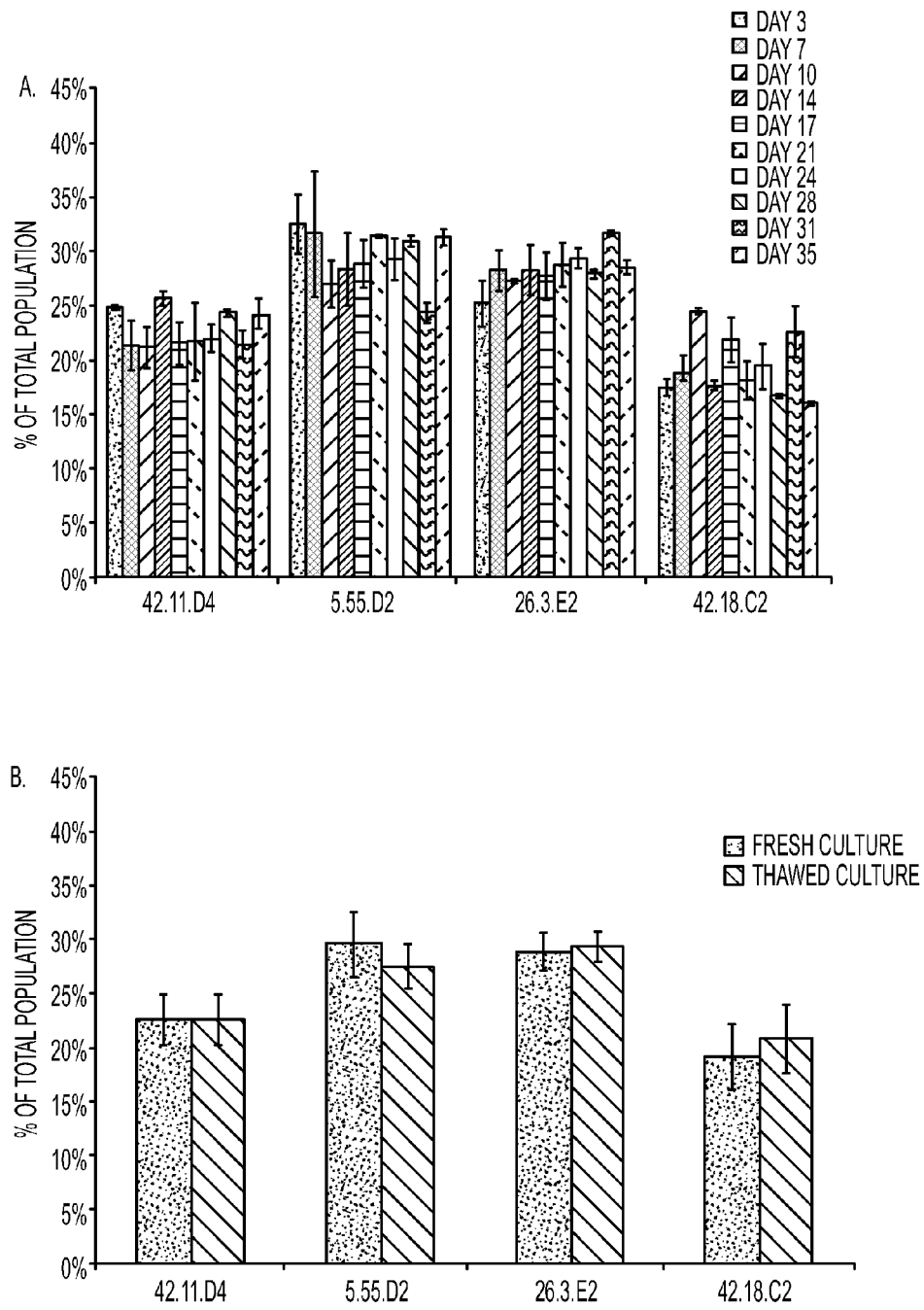
FIG. 6 shows a series of graphs demonstrating the reproducibility of polyclonal cell populations. (A) shows the ratio of component antibodies in polyclonal cell populations expressing four antibodies 42.11.D4, 5.55.D2, 26.3.E2 and 42.18.C2 over time. (B) shows the ratio of component antibodies of a polyclonal cell populations in fresh and frozen/thawed cultures.

IEX HPLC analysis of cell culture supernatants was performed Day 3, Day 7, Day 10, Day 14, Day 17, Day 21, Day 28, Day 31 and Day 35 as described above. The percentage of each antibody within duplicate cultures was average and the standard deviation is shown in FIG. 6A.

In this example, the relative differences between these duplicate cultures is minimal as is reflected by the data. There is no skewing or bias of any of the antibodies away from the mean. The standard deviations are reflective of the method of measurement in that they are larger when the total area underneath the HPLC peaks is smaller.

In a further experiment, a polyclonal population expressing antibodies, 42.11.D4, 5.55.D2, 26.3.E2 and 42.18.C2 was generated and divided as described above. One portion was kept in culture while the other was frozen and stored in liquid nitrogen. After one week, the frozen polyclonal population was thawed and allowed to recover. HPLC analysis of cell culture supernatants was performed on both the fresh polyclonal population and the thawed polyclonal population. The percentage of each antibody within the two populations over the same 17 day period was averaged and the standard deviation is shown in FIG. 6B.

The data indicate that the variation in the ratio of component antibodies within a polyclonal population is very small, if at all discernible, even when cultured independently or after having been held in cyrostorage. These results illustrate that polyclonal populations with specific and desirable characteristics can be stored and recovered with predictable outcomes.

E. Complex mixtures of antibodies can be purified from polyclonal populations.

Figure 7:
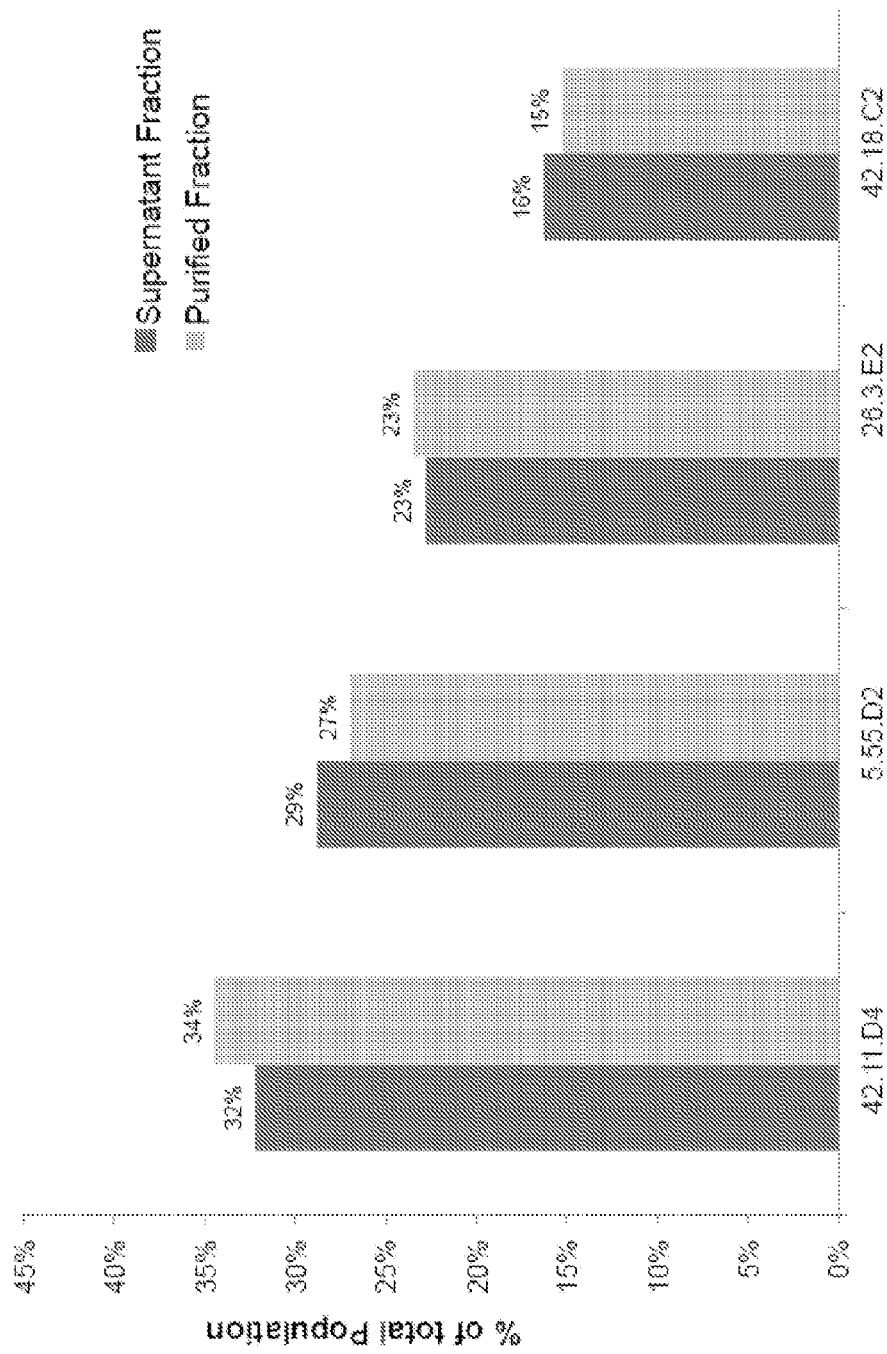
FIG. 7 is a graph demonstrating that complex mixtures of antibodies can be purified from polyclonal cell populations (e.g., compare supernatant factions (unpurified) with purified fractions).

The purpose of this example was to determine whether complex mixtures of antibodies can be consistently purified from polyclonal cell populations. The antibody population from the cell culture supernatant of a polyclonal population expressing antibodies 42.11.D4, 5.55.D2, 26.3.E2 and 42.18.C2 was purified using a Protein A-based capture protocol. IEX HPLC analysis of the purified antibody population was compared to the antibody population of the unpurified culture supernatants (FIG. 7). These results suggest that purification lead to efficient recovery of all of the different antibody elements within a polyclonal population. It was also observed that the relative standard deviation in samples decreased significantly as the volume of the sample was increased and the relative peak height was greater. This result suggests that the small differences in observed values from the HPLC profiles underlying all data from all these examples represent most likely the relative observed error than real changes in composition.

F. Polyclonal cell populations are stable in the absence of selective pressure

Figure 8:
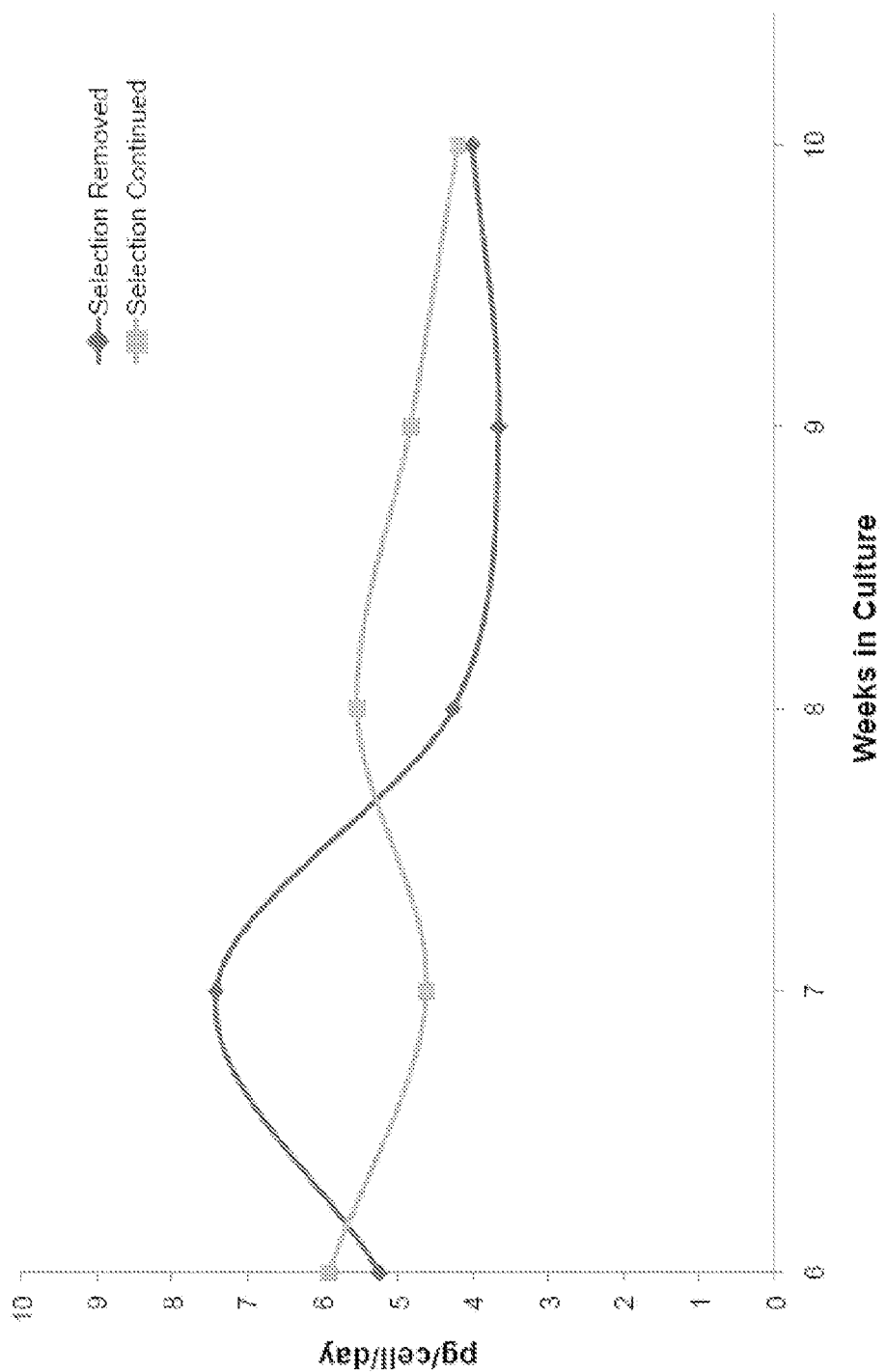
FIG. 8 is a graph demonstrating that polyclonal cell populations are stable in the absence of selective pressure to maintain the cell population (♦, selection with G418 was removed from the growth media; ■, cell population maintained with G418 in the growth media).

The stability of a cell population was tested in the absence of selective pressure. A cell population as described in FIG. 2 was established. After six weeks, the cell population expressing antibody 5.55.D2 was divided into two cultures. One continued to be cultured in the presence of the selective drug, G418 (■), while G418 was removed from growth media of the other (♦). Fc-specific ELISA of cell culture supernatant was performed twice a week. The total pg/ml of IgG1 at each time point was divided by the average cell number/day in culture and the average pg/cell/day for each week for both cultures is shown in FIG. 8. The data indicate that over a four week period no significant difference in IgG1 production was observed. This data suggests that the integration of the antibody producing vector in this cell population remains stable even in the absence of selection pressure.

G. AAV-rep dependant integration leads to increased antibody production

Figure 9:
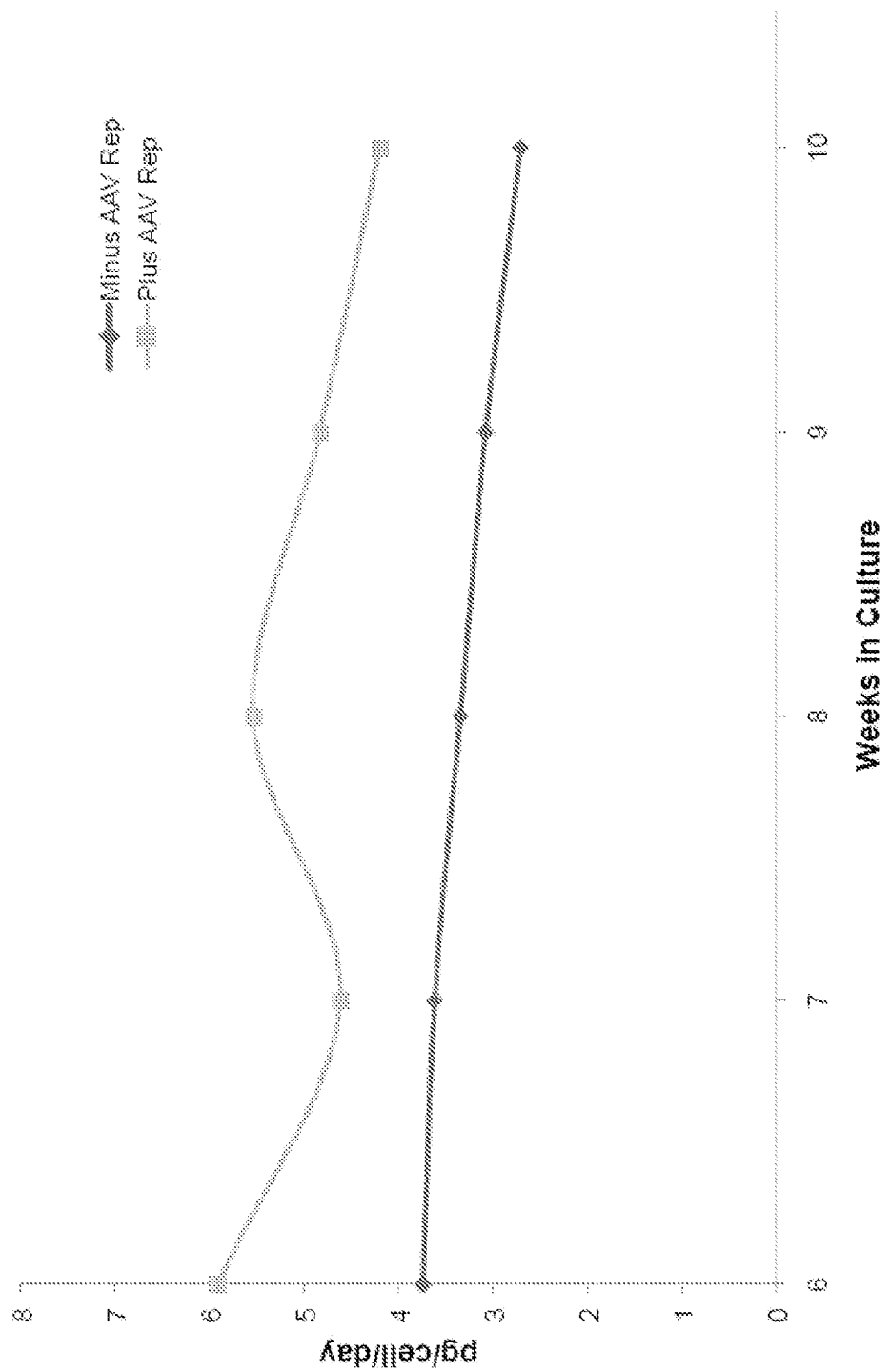
FIG. 9 is a graph demonstrating that AAV Rep dependent integration leads to enhances protein expression levels (♦, minus AAV Rep78 protein; ■, plus AAV Rep78 protein).

Freestyle 293 cells ($30 \times 10^6$) were transfected with 30 μg pExcel-ITR:5.55.D2 with or without 150 ng pAAV2-Rep78 using 293-Fectin. Three days post transfection, both transfected populations were passaged into growth media containing 500 μg/mL G418. Fc-specific ELISA of cell culture supernatant was performed twice a week. The total pg/ml of IgG1 at each time point was divided by the average cell number/day in culture and the average pg/cell/day for each week in selection is shown in FIG. 9.

In the absence of the Rep protein, the pExcel-ITR:5.55.D2 integrates via random integration. The relative production as measured in pg/cell/day is higher when the Rep protein mediates integration indicating that there is a qualitative difference between Rep mediated integration (which is a preferential integration as defined herein) and random integration (see, e.g., Smith, R H., Gene Therapy (2008) 15, 817-822, which describes that the Rep protein helps integrate ITR carrying plasmids into more expression permissive sites), In FIG. 9, as also described above for FIG. 2, the resulting populations are not clonal (i.e., are not cell lines), but in fact represent bulk populations likely made up of a diverse distribution of integration events. Both random and preferential integration can lead to a stably expressing population.

H. AAV-Rep Dependant Integration Leads to Increased Integration Events

Freestyle 293 cells ($2 \times 10^6$) were transfected with 2 μg the indicated vector system expressing antibody 5.55.D2 with 10 ng pAAV2-Rep78 using 293-Fectin. Cells were cultured for 17 days in the absence of any selection. Every 3 to 4 days the number of cells expressing antibody 5.55.D2 was assessed by FACS analysis. The percentage of cells expressing antibody 5.55.D2 on day 17 is shown.

Similar to the results shown in FIGS. 2 and 9, the resulting populations are not clonal but in fact represent bulk populations likely made up of a diverse distribution of integration events. Non-viral AAV mediated integration leads to an increase number of cells in the population which experience at least one integration event as compared to random integration (as shown in FIGS. 1 and 10). While random integration can be used to create a stable population expressing a protein of interest, the relative number of integrants and the quality of those integrants are less than that of a non-viral AAV mediated system (see, e.g., MigLiaccio et al., Gene 256 (2000) 197-214, which describes the relative instability of the majority of random integrants in a human genome).

Example 2

Production of Stable Polyclonal Cell Populations Using Retroviral Integrase to Promote Stable Expression of Exogenous DNA Sequences A. Retroviral Integrase promotes stable expression of exogenous DNA sequences in cultured cells.

The purpose of this experiment was to demonstrate that retroviral integrase promotes stable expression of exogenous DNA sequences in cultured cells.

Figure 18:
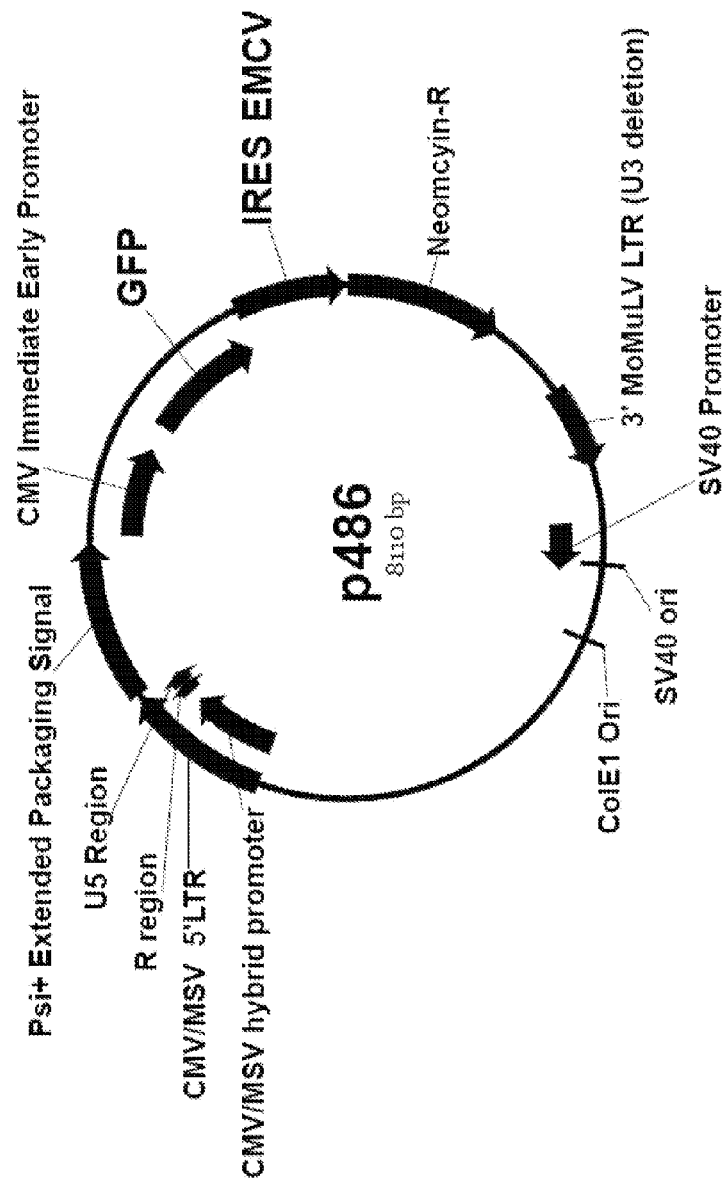
FIG. 18 is a schematic representation of a p486 vector, a retroviral vector comprising the following elements: CMV=CMV Immediate Early Promoter; GFP=GFP gene; IRES EMCV=encephalomyocarditis virus internal ribosome entry site; Neomycin-R=neomycin resistance gene; 3' MoMuLV LTR (U3 deletion)=3' long terminal repeat (LTR) region from Moloney Murine Leukemia virus with a deletion in the enhancer U3 region; SV40 Promoter=simian virus 40 promoter sequence; SV40 ori=simian virus 40 origin of replication; ColE1 Ori=colicin E1 origin of replication; CMV/MSV hybrid promoter, CMV/MSV 5'LTR, R region and U5 Region=components of a hybrid 5' long terminal repeat from cytomegalovirus and mouse sarcoma virus; Psi+Extended Packaging Signal=retroviral packaging signal.

GP2-293 cells (Clontech, Mountain View, Calif.), a retroviral packaging cell line, were co-transfected with p-VSV-G (Clontech), a vector that expresses the G glycoprotein of vesicular stomatitis virus (VSV-G), and p486 (FIG. 18), a modified pQCXIN vector (Clontech) containing GFP cloned from pEF/myc/nuc/GFP (Invitrogen, Carlsbad, Calif.).

FreeStyle 293F (Invitrogen) cells were transduced with the resulting retroviral particles containing GFP at 48 hours post-transfection. The transduced cells were continuously sub-cultured in the absence of antibiotic selection, and the transduction efficiency was periodically assayed via FACS using a Guava easyCyte 8HT (EMD Millipore, Billerica, Mass.).

Figure 11:
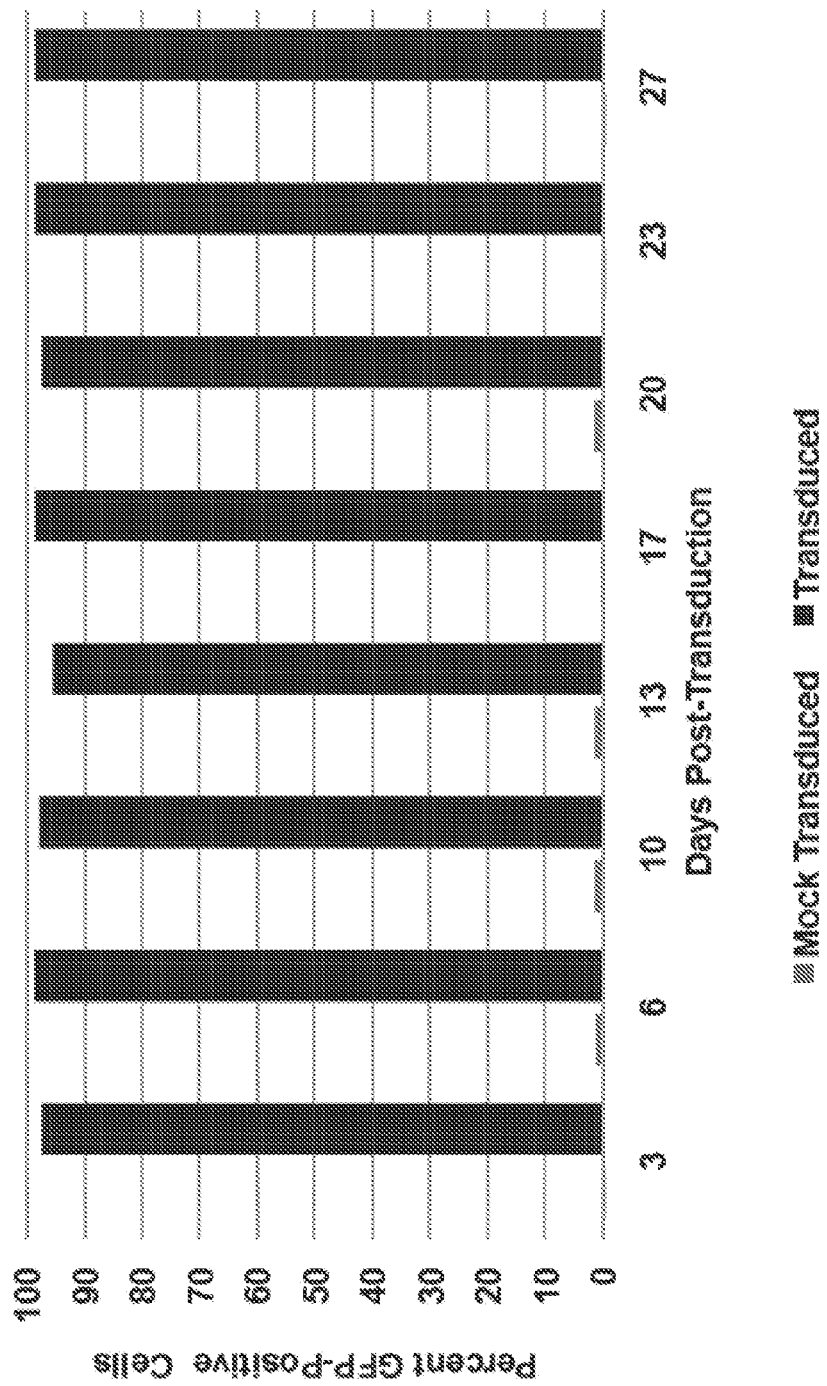
FIG. 11 is a graph showing the consistent expression of GFP in transduced FreeStyle 293F cells using retroviral integrase over 27 days.

The graph in FIG. 11 shows the average percent GFP-positive cells from replicate cultures. The data indicate that the percent positive GFP-expressing cells remains consistent over the time period indicated and the transduction efficiency shows that greater than 95% of cells are stably GFP positive after a single transduction. The data also indicate that in the absence of antibiotic selection a stable integrant population can be maintained even in the presence of cells not having integrants. Thus, cell populations can be generated and maintained with a majority of such cells having one or more integrations into their genomic DNA, but also having a subset of cells where no integration has occurred. This non-transformed subset (e.g., cells where there was no integration of a DNA fragment) of the population is not more evolutionarily fit and does not change the overall proportion of cells in the cell population over time (e.g., no skewing or bias is observed where the non-integrants (or, alternatively, the integrant population becomes more prominent). The data obtained with cell populations as described herein indicate that the disclosed cell populations behave differently from mixed individual cell lines. For example, cell lines (e.g., MigLiaccio et al., Gene 256 (2000) 197-214), and mixed cell lines are frequently unstable. Surprisingly, the data disclosed herein demonstrate that polyclonal cell populations are stable over time.

B. Production of Stable Polyclonal Cell Populations Using Retroviral Integrase

The purpose of this experiment was to generate stable polyclonal cell populations expressing antibodies using retroviral integrase.

Figure 19:
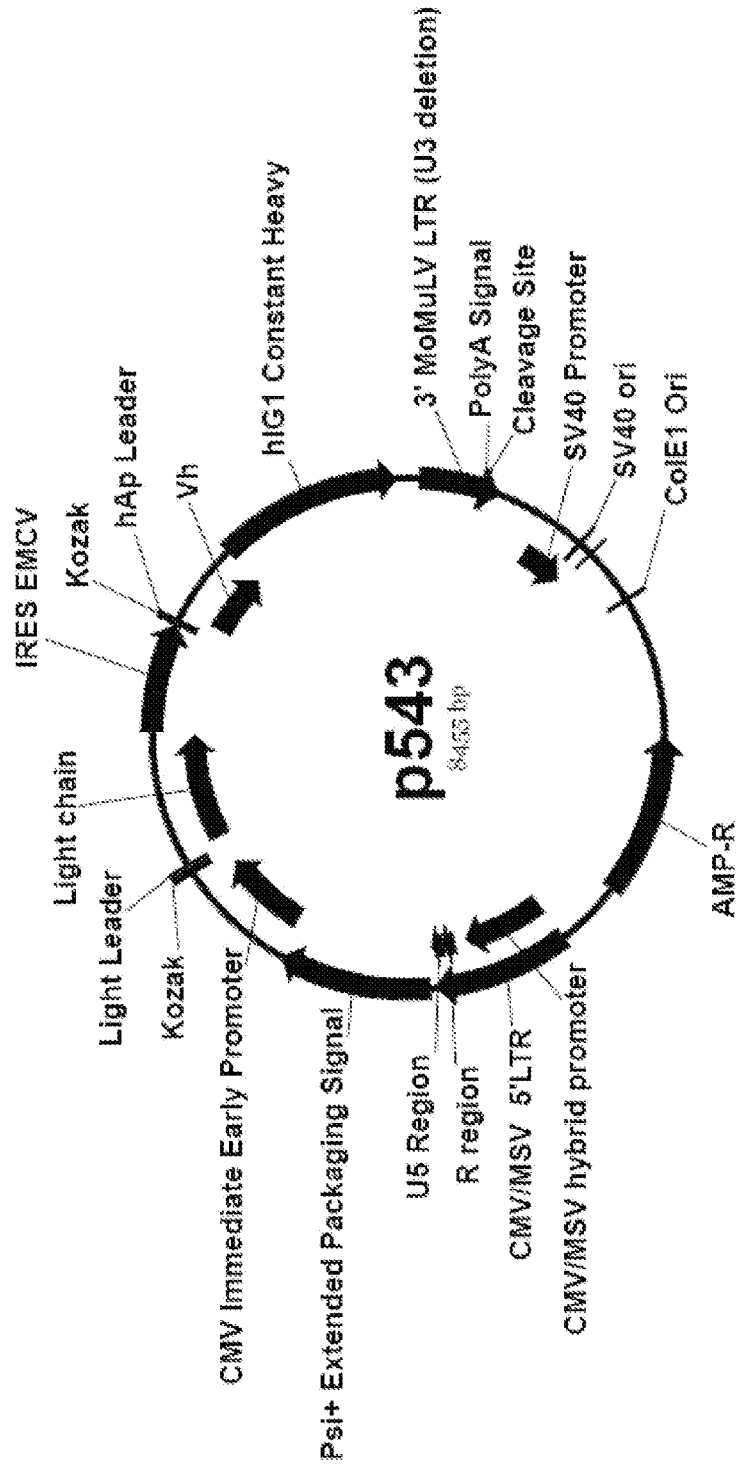
FIG. 19 is a schematic representation of p543, a retroviral vector comprising the following elements: CMV=CMV Immediate Early Promoter; GFP=GFP gene; IRES EMCV=encephalomyocarditis virus internal ribosome entry site; 3' MoMuLV LTR (U3 deletion)=3' long terminal repeat (LTR) region from Moloney Murine Leukemia virus with a deletion in the enhancer U3 region; SV40 Promoter=simian virus 40 promoter sequence; SV40 ori=simian virus 40 origin of replication; ColE1 Ori=colicin E1 origin of replication; CMV/MSV hybrid promoter, CMV/MSV 5'LTR, R region and U5 Region=components of a hybrid 5' long terminal repeat from cytomegalovirus and mouse sarcoma virus; Psi+Extended Packaging Signal=retroviral packaging signal; light leader=a human kappa leader sequence; light chain=Variable and constant regions of either lambda or kappa antibody of interest, flanked by restriction sites; hAp leader=human Alkaline phosphastase leader sequence; Variable Heavy Chain=Variable region of the heavy chain of the antibody of interest, flanked by restriction sites; hIG1 Constant Heavy=cDNA of the human IgG1 constant region.

GP2-293 cells (Clontech), a retroviral packaging cell line, were co-transfected with p-VSV-G (Clontech), a vector that expresses the G glycoprotein of vesicular stomatitis virus (VSV-G), and a modified pQCXIN vector (Clontech) containing antibody heavy and light chain, see example vector p543 (FIG. 19). FreeStyle 293F (Invitrogen) cells were transduced with the resulting retroviral particles containing each of the following antibodies at 48 hours post-transfection: 5.55D2, 26.3E2, 42.11D4, or 42.18C2. The transduced cells were continuously sub-cultured.

Figure 12:
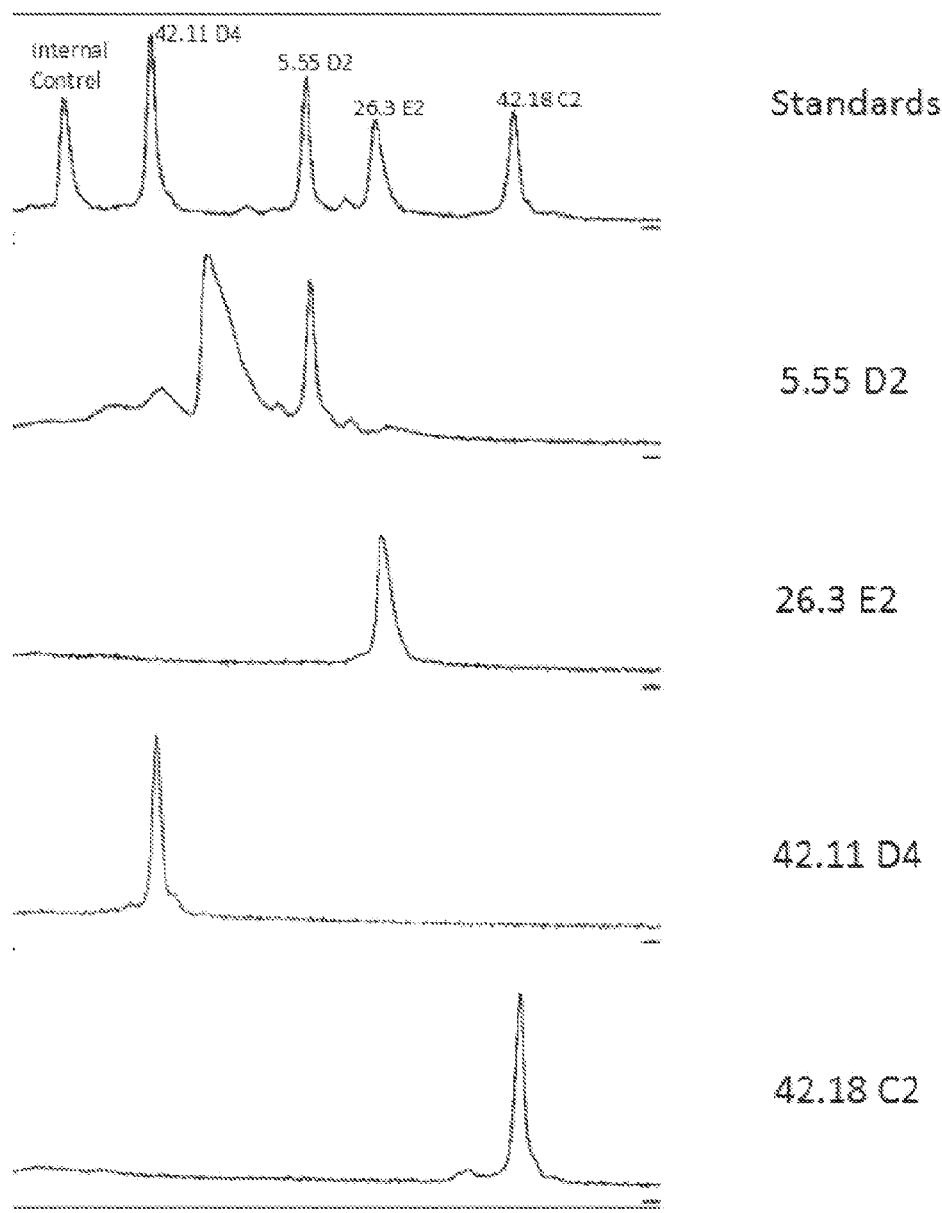
FIG. 12 is a series of HPLC chromatographs showing the individual antibody components (e.g., antibodies 42.11.D4, 5.55.D2, 26.3.E2 and 42.18.C2) of a polyclonal cell population produced using retroviral integrase.

Culture supernatants were removed 10 days post-transduction and analyzed via HPLC. The top chromatogram represents the standard, a mixture of purified antibodies that correspond to the antibodies produced by the retroviral vector system. The four subsequent chromatograms represent the analysis of the culture supernatants containing an antibody (as indicated in FIG. 12) produced using the retroviral vector system. As shown in FIG. 12, the antibody proteins eluted from the HPLC column at distinct retention times. In addition, the antibodies produced using the retroviral vector system and the corresponding antibody from the standard antibody mix show comparable retention times. In the chromatogram labeled 5.55D2, one peak corresponds to the full-length 5.55D2 antibody in the standard antibody mix. The second peak, which has a shorter retention time, may represent excess production of antibody lambda light chain.

This example demonstrates that a balanced antibody expression vector can be stably integrated into a host cell genomic DNA. Persons skilled in the art would understand that the balance of heavy and light chain is not always straightforward and has to be calibrated. For example, for the IRES containing construct depicted in FIG. 19, heavy and light chain balance was present in 3 out of 4 antibodies. In order to obtain balance, there are various options using retroviral vectors or components thereof. One option is to select for a cell line which shows perfect balance with multiple integrations per cell using single chain vectors (see, e.g., U.S. Pat. No. 6,852,510). Alternatively, the IRES element present in FIG. 19 can be replaced with another element, such as a promoter element. One such construct where the IRES was replaced by a promoter has been successful in yielding the 5.55.D2 antibody without the additional putative lambda light chain excess. In addition, a 2A/furin cleavage site can be used (Jostock et al., Appl Microbiol Biotechnol (2010) 87:1517-1524). Alternatively, a DNA plasmid vector can be used, e.g., as depicted in FIG. 15 wherein the ITR elements are replaced with LTR elements and a cloned Retroviral Integrase gene is used instead of the Rep protein (Rep containing plasmid depicted in FIG. 17).

Figure 20:
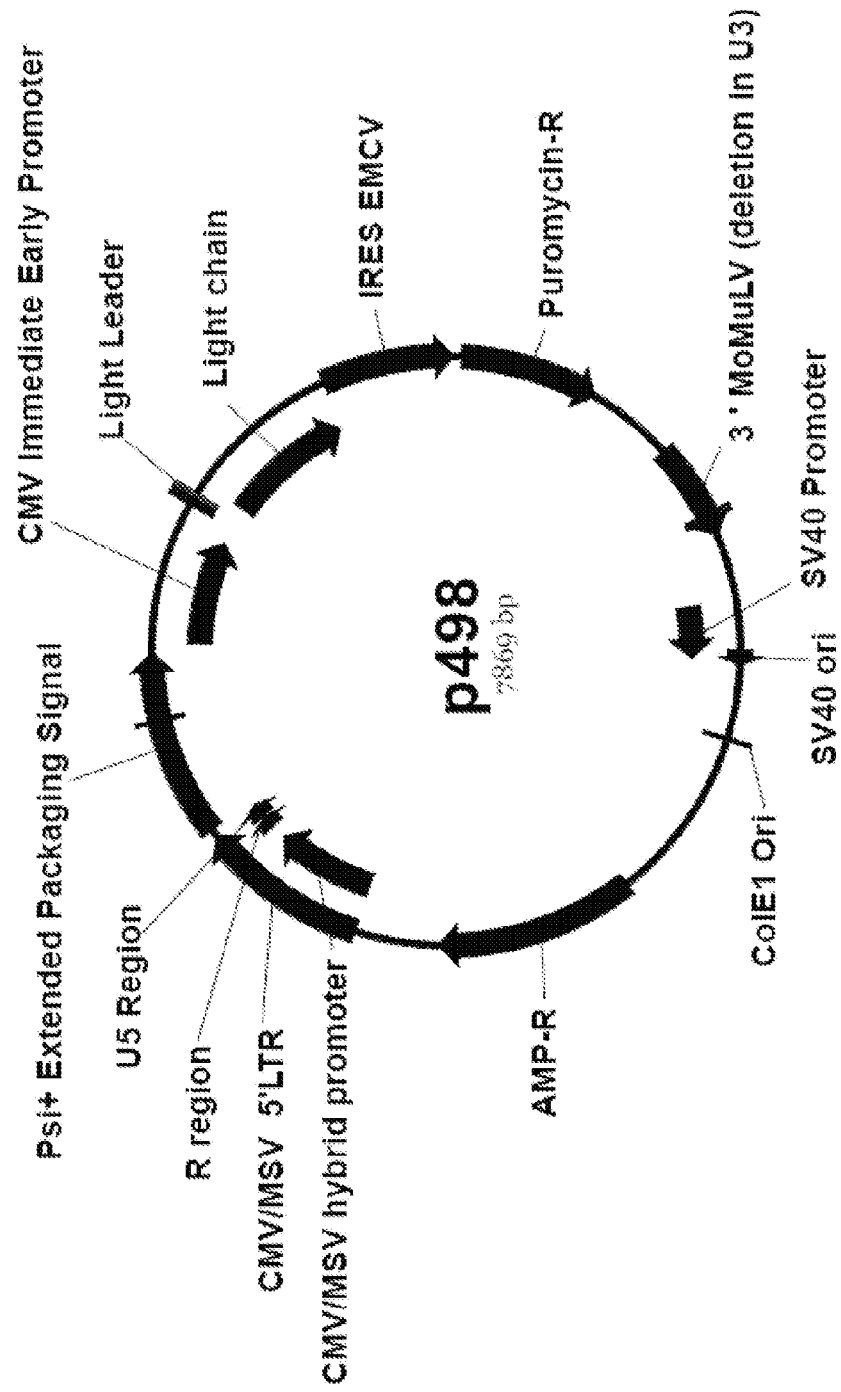
FIG. 20 is a schematic representation of p498, a retroviral vector comprising the following elements: CMV=CMV Immediate Early Promoter; light leader=a human kappa leader sequence; light chain=Variable and constant regions of either lambda or kappa antibody of interest, flanked by restriction sites; hAp leader=human Alkaline phosphastase leader sequence; IRES EMCV=encephalomyocarditis virus internal ribosome entry site; Puromycin-R=puromycin resistance gene; 3' MoMuLV LTR (U3 deletion)=3' long terminal repeat (LTR) region from Moloney Murine Leukemia virus with a deletion in the enhancer U3 region; SV40 Promoter=simian virus 40 promoter sequence; SV40 ori=simian virus 40 origin of replication; ColE1 Ori=colicin E1 origin of replication; CMV/MSV hybrid promoter, CMV/MSV 5'LTR, R region and U5 Region=components of a hybrid 5' long terminal repeat from cytomegalovirus and mouse sarcoma virus; Psi+Extended Packaging Signal=retroviral packaging signal.

In a separate experiment, the transduction efficiency of Freestyle 293F cells transduced with antibody light chain was also tested. As described above, GP2-293 cells (Clontech), a retroviral packaging cell line, were co-transfected with p-VSV-G (Clontech), a vector that expresses the G glycoprotein of vesicular stomatitis virus (VSV-G), and a modified pQCXIN vector (Clontech) containing antibody light chain, see example p498 (FIG. 20). FreeStyle 293F (Invitrogen) cells were transduced with the resulting retroviral particles containing light chains from antibodies 5.55D2, 26.3E2, 42.11D4, or 42.18C2 at 48 hrs post-transfection. The transduced cells were continuously subcultured in the absence of antibiotic selection.

At days 4 and 7 post-transduction, cells were fixed and permeabilized using the FIX & PERM reagents as per manufacturers instructions (Invitrogen), and stained for lambda or kappa light chain using FITC-conjugated mouse anti-human light chain lambda or kappa antibodies (BioLegend, San Diego, Calif.). The transduction efficiencies were assayed via FACS using a Guava easyCyte 8HT (EMD Millipore). The average percent of FITC-stained lambda or kappa light chain or mock transduced cells is shown FIG. 13. From FIG. 13, the transduction efficiencies either increased between days 4 and 7, or stayed within standard error. Representative FACS side versus forward scatter plots and green fluorescence histograms are presented in FIG. 13B for days 4 and 7 (FIG. 13B) post-transduction of a lambda antibody (5.55D2) and kappa antibody (26.3E2).

Figure 13A:
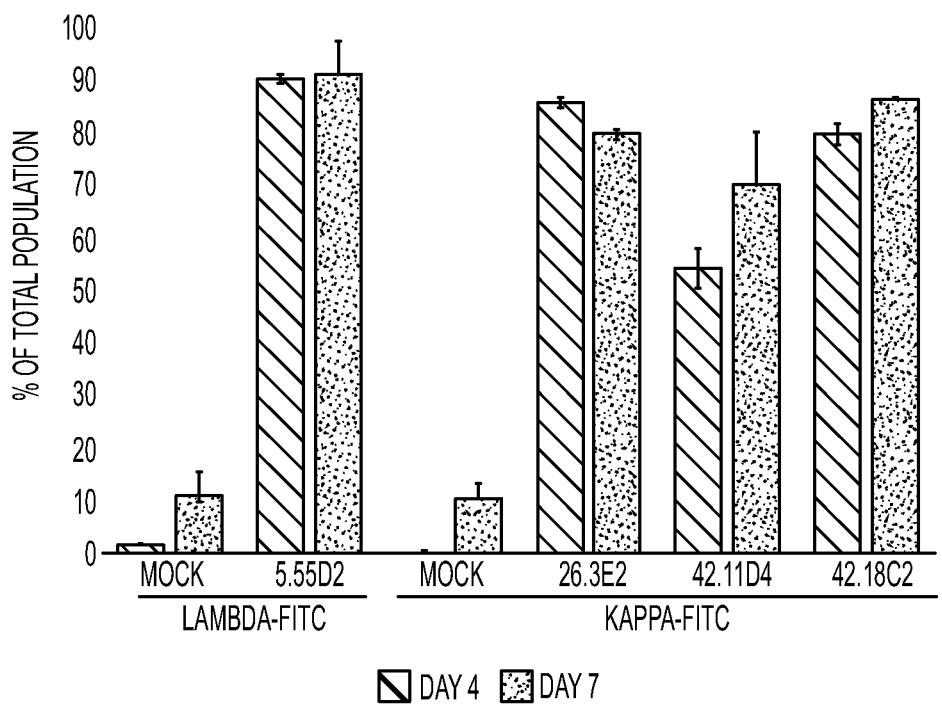
FIG. 13 shows a graph (A) and a series of chromatograms (B) showing the level of transduction efficiency of antibody vectors and their individual expressed antibody profiles. (A) a graph showing the percent average of FITC positive stained FreeStyle 293F cells 4 and 7 days post-transduction with retroviral integrase. (B) is a series of FACS scatter plots and FITC-histograms days 4 and 7 postranduction of a lambda antibody (5.55.D2) and a kappa antibody (26.3.E2).
Figure 13B:
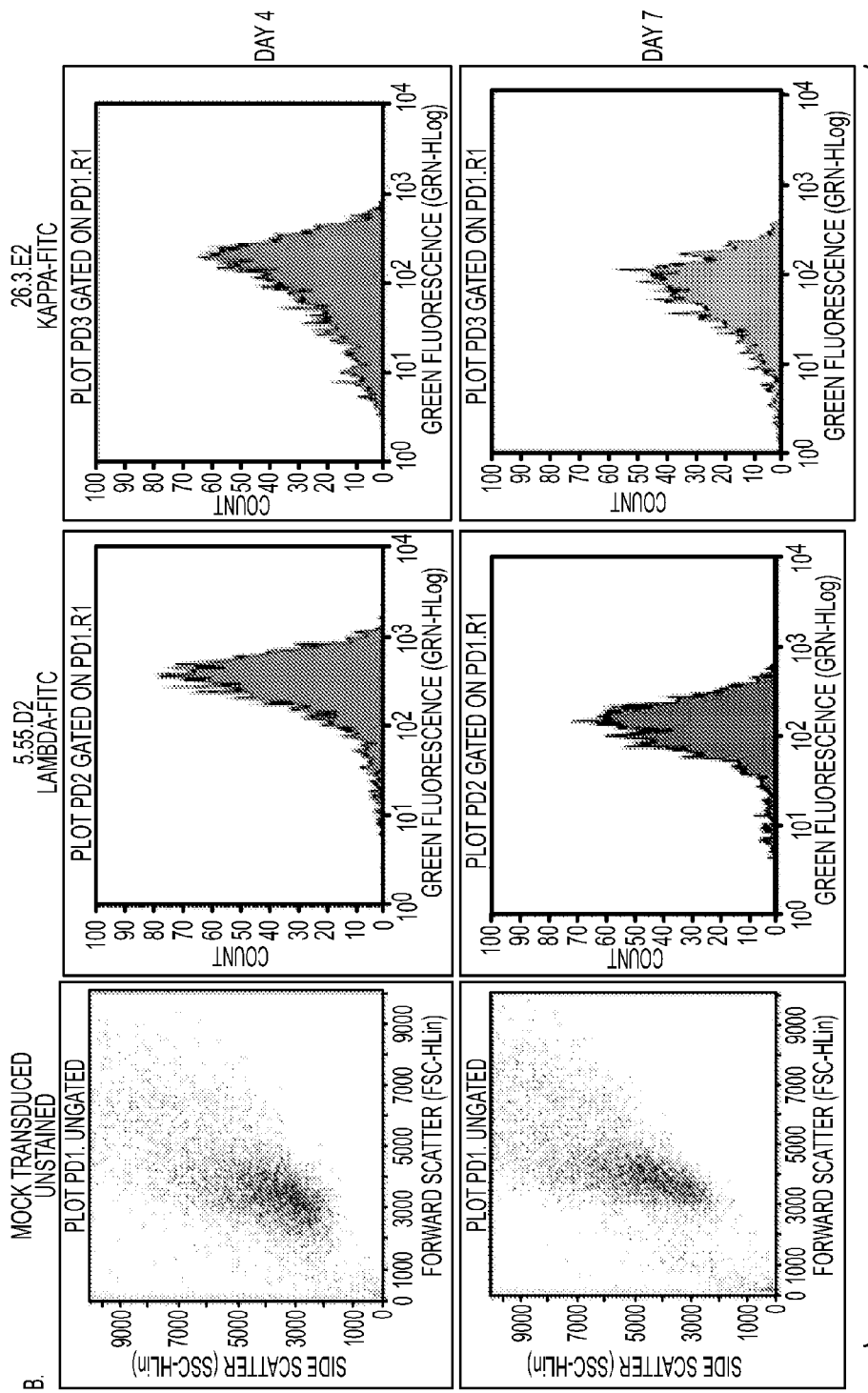

FIG. 13 shows that antibody chains, i.e., immunoglobulin light chains, can be transformed into cell populations at rates approximating the GFP constructs shown in FIG. 11. Thus, a vector carrying an antibody heavy chain can be subsequently transformed into these cell populations to make a complete antibody comprising both a heavy chain and a light chain.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and the range of equivalency of the claims are intended to be embraced therein.

What is claimed is:

1. A method for producing a polyclonal cell population, said method comprising the steps of:
   a) transforming one or more host cells with at least one vector comprising at least one copy of a nucleic acid sequence that encodes a component of a polyclonal protein composition, in the presence of a recombinase or retroviral integrase, such that the at least one vector integrates into the host cell genome at a plurality of locations recognized by the recombinase or retroviral integrase;
   b) generating a cell population capable of producing the component of the polyclonal protein composition; and
   c) mixing the cell population and a different cell population producing a different component of the polyclonal protein composition generated by performing steps (a) and (b) to produce a polyclonal cell population capable of producing the polyclonal protein composition.

2. The method of claim 1, wherein the cell population generated in step b comprises transformed host cells and non-transformed host cells.

3. The method of claim 2, further comprising after step b, selecting the cell population of transformed host cells.

4. The method of claim 1, wherein the vector is an adeno-associated viral (AAV) vector or a retroviral vector.

5. The method of claim 1, wherein the polyclonal protein composition comprises a polypeptide comprising an immunoglobulin heavy chain variable region and a polypeptide comprising an immunoglobulin light chain variable region that together bind a specific antigenic epitope.

6. The method of claim 1, wherein the polyclonal protein composition comprises two polypeptides that together form a T cell receptor (TCR).

7. The method of claim 6, wherein the two polypeptides that together form a TCR comprise a polypeptide comprising an alpha chain of a TCR and a polypeptide comprising a beta chain of a TCR.

8. The method of claim 6, wherein the two polypeptides that together form a TCR comprise a polypeptide comprising a gamma chain of a TCR and a polypeptide comprising a delta chain of a TCR.

9. The method of claim 1, wherein the at least one vector encodes an infectious agent of a pathogen or isoform thereof.

10. The method of claim 1, wherein each cell population mixed in step (c) comprises greater than about 10,000 individual cells.

11. The method of claim 1, wherein the polyclonal cell population produced in step (c) comprises at least a hundred thousand cells, at least one million cells, or at least 10 million cells.

12. The method of claim 1, wherein in step (c), the cell population and the different cell population are mixed at a 1:1 ratio.

13. The method of claim 1, wherein after step (b), the cell population produced by steps (a)-(b) is not banked.

14. The method of claim 1, further comprising purifying the polyclonal protein composition from the polyclonal cell population produced in step (c).

15. The method of claim 1, wherein the polyclonal cell population comprises at least three, five, ten, fifteen, twenty, twenty-five, or fifty cell populations each capable of producing a different protein.

16. The method of claim 1, wherein the cell population generated by performing steps (a) and (b) is capable of producing at least two, five, or ten different components of the polyclonal protein composition.

17. The method of claim 1, wherein the transformation of the one or more host cells does not require clonal selection of an individual progenitor cell clone or the production of a cell line.

18. The method of claim 1, wherein one or more host cells are transformed with a library of vectors.

19. The method of claim 18, wherein the library of vectors encode multimeric proteins.

20. The method of claim 19, wherein the multimeric proteins comprise a polypeptide comprising an immunoglobulin heavy chain variable region and a polypeptide comprising an immunoglobulin light chain variable region that together bind a specific antigenic epitope.

21. The method of claim 1, wherein the recombinase is an AAV rep protein.

22. The method of claim 21, wherein the AAV rep protein is provided to the host cell in a packaging cell line, on another DNA vector, as a mRNA, or as a recombinant protein.

23. The method of claim 1, wherein the AAV rep protein is rep78.

24. The method of claim 1, further comprising, after step c, selecting a subset of transformed host cells in the polyclonal cell population.

25. The method of claim 1, where each cell population produces at least 3 pg/cell/day of its component over at least an 11 week period.

26. The method of claim 1, wherein the percentage of each cell population in the polyclonal cell population does not vary by more than 20% for at least 35 days from mixing.

27. The method of claim 1, wherein the host cells are CHO cells.

28. The method of claim 1, wherein step (b) comprises a selection process to identify individual progenitor cells followed by clonal expansion of individual cell lines.

29. The method of claim 1, wherein in step (a), the host cell is transformed with the at least one vector at least twice or at least five times.

30. A method for producing a polyclonal cell population, said method comprising the steps of:
   a) transforming one or more host cells with at least one adeno-associated viral (AAV) vector comprising at least one copy of a nucleic acid sequence, in the presence of an AAV rep protein, such that the at least one AAV vector integrates into the host cell genome at a plurality of locations recognized by the AAV rep protein and that encodes a component of a polyclonal protein composition;
   b) generating a cell population capable of producing the component of the polyclonal protein composition; and
   c) mixing the cell population and a different cell population capable of producing a different component of the polyclonal protein composition generated by performing steps (a) and (b) to produce a polyclonal cell population capable of producing the polyclonal protein composition.

31. The method of claim 30, wherein the AAV rep protein is AAV Rep78.

32. The method of claim 30, wherein the transformation of the one or more host cells does not require clonal selection of an individual progenitor cell clone or the production of a cell line.

33. The method of claim 30, wherein the host cells are CHO cells.

34. The method of claim 30, wherein step (b) comprises a selection process to identify individual progenitor cells followed by clonal expansion of individual cell lines.

* * * * *

UNITED STATES PATENT AND TRADEMARK OFFICE
CERTIFICATE OF CORRECTION

PATENT NO. : 9,447,174 B2  
APPLICATION NO. : 14/037833  
DATED : September 20, 2016  
INVENTOR(S) : Coljee et al.

Page 1 of 1

It is certified that error appears in the above-identified patent and that said Letters Patent is hereby corrected as shown below:

In the Claims

Column 38, Lines 63 and 64 (Claim 23), please replace:
"The method of claim 1, wherein the AAV rep protein is rep78."

With:
--The method of claim 21, wherein the AAV rep protein is rep78.--

Signed and Sealed this
Seventh Day of November, 2017

Joseph Matal
*Performing the Functions and Duties of the
Under Secretary of Commerce for Intellectual Property and
Director of the United States Patent and Trademark Office*